(12) United States Patent
Noh et al.

(10) Patent No.: US 10,043,986 B2
(45) Date of Patent: Aug. 7, 2018

(54) ORGANOMETALLIC COMPOUND AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Changho Noh, Suwon-si (KR); Rupasree Ragini Das, Suwon-si (KR); Kangmun Lee, Suwon-si (KR); Virendra Kumar Rai, Hwaseong-si (KR); Dmitry Kravchuk, Hwaseong-si (KR)

(73) Assignees: SAMSUNG ELECTRONICS CO., LTD., Gyeonggi-Do (KR); SAMSUNG SDI CO., LTD., Gyeonggi-Do (KR)

(*) Notice: Subject to any disclaimer, the term of this patent is extended or adjusted under 35 U.S.C. 154(b) by 485 days.

(21) Appl. No.: 14/680,488

(22) Filed: Apr. 7, 2015

(65) Prior Publication Data
US 2015/0322102 A1    Nov. 12, 2015

(30) Foreign Application Priority Data

May 7, 2014   (KR) .................. 10-2014-0054431

(51) Int. Cl.
*H01L 51/00* (2006.01)
*C07F 15/00* (2006.01)
(Continued)

(52) U.S. Cl.
CPC ...... *H01L 51/0085* (2013.01); *C07F 15/0033* (2013.01); *H01L 51/5004* (2013.01);
(Continued)

(58) Field of Classification Search
CPC ............. H01L 51/0085; H01L 51/5016; H01L 51/5004; H01L 51/5056; H01L 51/5088;
(Continued)

(56) References Cited

U.S. PATENT DOCUMENTS 7,585,573 B2 *  9/2009  Lee ................ C07F 15/0033
                                                    252/301.16
2014/0158998 A1   6/2014  Noh et al.
(Continued)

FOREIGN PATENT DOCUMENTS

CN   102558238 A  *  7/2012
CN   102899023 A     1/2013
(Continued)

OTHER PUBLICATIONS

Virendra Kumar Rai et al. "Synthesis, structure and efficient electroluminescence of a heteroleptic dipyridylamido/bis (pyridylphenyl)iridium(III) complex", Chem. Commun., 2011, 47, 5726-5728.

*Primary Examiner* — Michael M Bernshteyn
(74) *Attorney, Agent, or Firm* — Cantor Colburn LLP

(57) ABSTRACT

An organometallic compound represented by Formula 1:

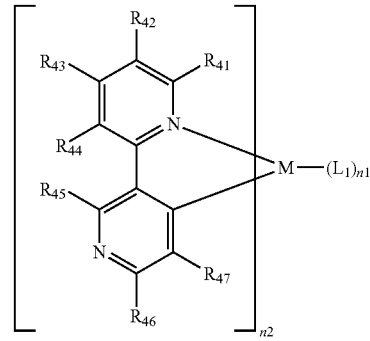

Formula 1 wherein in Formula 1, M, $L_1$, n1, n2, and $R_{41}$ to $R_{47}$ are described in the specification.

19 Claims, 1 Drawing Sheet

(51) Int. Cl.
*H01L 51/50* (2006.01)
*H01L 51/52* (2006.01)

(52) U.S. Cl.
CPC ...... *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5206* (2013.01); *H01L 2251/308* (2013.01); *H01L 2251/552* (2013.01)

(58) Field of Classification Search
CPC ............. H01L 51/5072; H01L 51/5096; H01L 51/5092; H01L 2251/308; H01L 2251/552; C07F 15/0033
USPC ........................................................ 428/690
See application file for complete search history.

(56) References Cited

U.S. PATENT DOCUMENTS

| | | | |
|---|---|---|---|
| 2015/0086903 A1 | | 3/2015 | Yoo |
| 2015/0194612 A1* | | 7/2015 | Tsai .................... H01L 51/0085 257/40 |
| 2015/0221878 A1* | | 8/2015 | Rai .................... H01L 51/0085 257/40 |
| 2015/0249222 A1* | | 9/2015 | Szigethy ................ C09K 11/06 257/40 |

FOREIGN PATENT DOCUMENTS

| | | | | |
|---|---|---|---|---|
| CN | 102899024 A | * | 1/2013 | |
| CN | 103666449 A | * | 3/2014 | |
| JP | WO 2012074022 A1 | * | 6/2012 | .......... C07F 15/0033 |
| WO | 2012074022 A1 | | 6/2012 | |

* cited by examiner

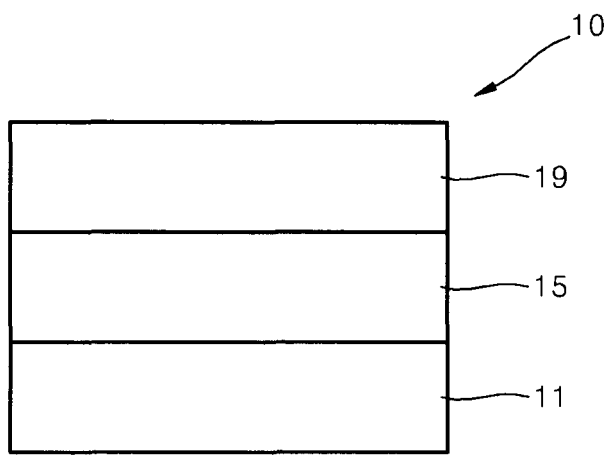

ORGANOMETALLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2014-0054431, filed on May 7, 2014 in the Korean Intellectual Property Office, and all the benefits accruing therefrom under 35 U.S.C. § 119, the content of which is incorporated herein in its entirety by reference.

BACKGROUND

1. Field

One or more embodiments of the present disclosure relate to an organometallic compound and an organic light-emitting device including the organometallic compound.

2. Description of the Related Art

Organic light-emitting devices (OLEDs) are self-emitting devices that can provide multicolored images and have advantages such as wide viewing angles, excellent contrast, quick response times, excellent brightness, low driving voltages, and excellent response speed characteristics.

A typical OLED has a structure including an anode, a cathode, and an organic layer disposed between the anode and the cathode and including an emission layer (EML). A hole transporting region may be disposed between the anode and the EML, and an electron transporting region may be formed between the EML and the cathode. Holes injected from the anode move to the EML via the hole transport region, and electrons injected from the cathode move to the EML via the electron transport region. Excitons are generated when carriers such as holes and electrons recombine in the EML. When the excitons drop from an excited state to a ground state, light is emitted.

Various types of organic light emitting devices are known. However, there still remains a need in OLEDs having low driving voltage, high efficiency, high brightness, and long lifespan.

SUMMARY

One or more embodiments include a novel organometallic compound and an organic light-emitting device including the novel organometallic compound.

Additional aspects will be set forth in part in the description which follows and, in part, will be apparent from the description, or may be learned by practice of the presented embodiments.

According to one or more embodiments, provided is an organometallic compound represented by Formula 1, wherein $L_1$ in Formula 1 includes at least one selected from a first ligand represented by Formula 2A, a second ligand represented by Formula 2B, and a third ligand represented by one selected from Formulae 2C, 2D, and 2E:

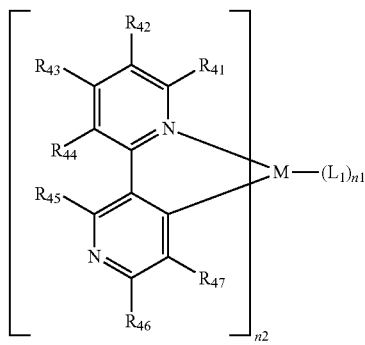

Formula 1

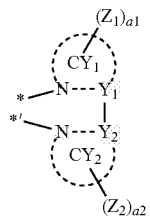

Formula 2A

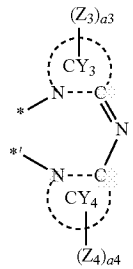

Formula 2B

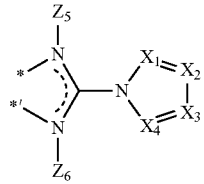

Formula 2C

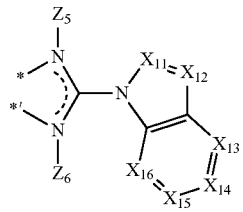

Formula 2D

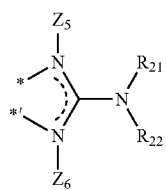

Formula 2E

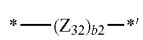

Formula 3 wherein, in Formulae 1, 2A to 2E, and 3 above,

M is selected from Ir, Pt, Os, Ti, Zr, Hf, Eu, Tb, and Tm;

$CY_1$ to $CY_4$ may be each independently a $C_2$-$C_{60}$ heterocyclic group including at least one N;

$Y_1$ and $Y_2$ may be each independently selected from C or N;

$X_1$ may be N or $CR_1$,
$X_2$ may be N or $CR_2$,
$X_3$ may be N or $CR_3$,
$X_4$ may be N or $CR_4$,
$X_{11}$ may be N or $CR_{11}$,
$X_{12}$ may be N or $CR_{12}$,
$X_{13}$ may be N or $CR_{13}$,
$X_{14}$ may be N or $CR_{14}$,
$X_{15}$ may be N or $CR_{15}$, and
$X_{16}$ may be N or $CR_{16}$;

$Z_{32}$ may be selected from *—O—*', *—S—*', *—N$(Q_{51})$—*', *—$C(Q_{52})(Q_{53})$—*', *—$C(Q_{54})$=$C(Q_{55})$—*', and

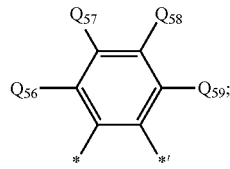

b2 may be an integer selected from 1 to 10 and when b2 is 2 or greater, groups $Z_{32}$ may be the same or different;

$R_{41}$ to $R_{47}$, $Z_1$ to $Z_6$, $R_1$ to $R_4$, $R_{11}$ to $R_{16}$, and $Q_{51}$ to $Q_{59}$ may be each independently selected from a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$O_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, and —$B(Q_6)(Q_7)$;

$R_{21}$ and $R_{22}$ may be each independently selected from a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed heteropolycyclic group;

$R_{21}$ and $R_{22}$ may optionally bind to each other via single bond or a second linking group represented by Formula 3;

the following conditions regarding $R_{21}$ and $R_{22}$ in Formula 2E are excluded
i) where $R_{21}$ and $R_{22}$ are both phenyl groups,
ii) where $R_{21}$ and $R_{22}$ are both phenyl groups substituted with a tert-butyl group,
iii) where $R_{21}$ and $R_{22}$ are both ethyl groups,
iv) where $R_{21}$ and $R_{22}$ are both propyl groups,
v) where $R_{21}$ and $R_{22}$ are both butyl groups, and
vi) where $R_{21}$ and $R_{22}$ are both —$Si(CH_3)_3$;

in Formula 1, both $R_{45}$ and $R_{46}$ are not —F;
in Formula 1, when $L_1$ includes the second ligand or the third ligand, each of $R_{41}$ to $R_{47}$ is not a hydrogen;
in Formula 2D, at least one selected from $X_{11}$ to $X_{16}$ is N;
a1 to a4 may be each independently integers selected from 1 to 5;
n1 may be an integer selected from 0 to 2;
n2 may be an integer selected from 1 to 3;
* and *' are binding sites to M in Formula 1;
in Formula 2A, a bond between N and $Y_1$ and a bond between N and $Y_2$, and in Formula 2B, a bond between C and N may be each independently a single bond or a double bond;

at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, monovalent non-aromatic condensed polycyclic group, monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$) and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$); wherein, $Q_1$ to $Q_7$, $Q_{11}$ to $Q_{17}$, $Q_{21}$ to $Q_{27}$ and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

According to another embodiment, provided is an organic light-emitting device including a first electrode;

a second electrode; and an organic layer including an emission layer (EML) disposed between the first electrode and the second electrode, wherein the emission layer includes an organometallic compound represented by Formula 1.

The organometallic compound may be included in the EML, the organometallic compound included in the EML may act as a dopant, and the EML may further include a host.

BRIEF DESCRIPTION OF THE DRAWINGS

These and/or other aspects will become apparent and more readily appreciated from the following description of the embodiments, taken in conjunction with the accompanying drawing, in which the FIGURE is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

An organometallic compound may be represented by Formula 1. In Formula 1 below, $L_1$ may include at least one selected from a first ligand represented by Formula 2A below, a second ligand represented by Formula 2B below, and a third ligand represented by one selected from Formulae 2C, 2D, and 2E:

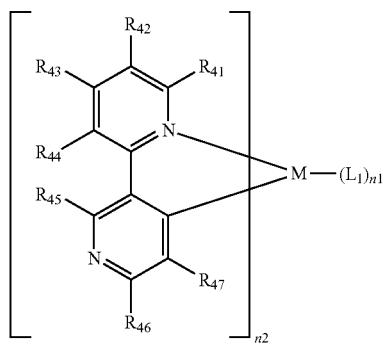

Formula 1

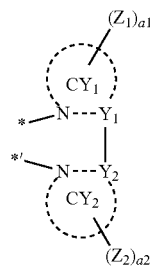

Formula 2A

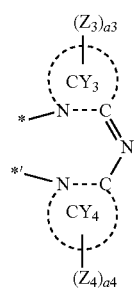

Formula 2B

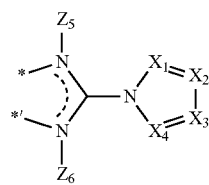

Formula 2C

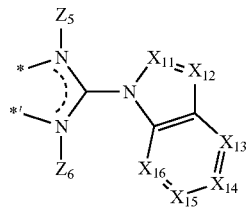

Formula 2D

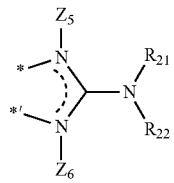

Formula 2E

In the Formulae above, * and *' are binding sites to M in Formula 1 above.

In Formula 1, M may be selected from iridium (Ir), platinum (Pt), osmium (Os), titanium (Ti), zirconium (Zr), hafnium (Hf), europium (Eu), terbium (Tb), and thulium (Tm).

For example, in Formula 1, M may be Ir or Pt.

In Formulae 2A and 2B, $CY_1$ to $CY_4$ may be each independently a $C_2$-$C_{60}$ heterocyclic group including at least one N.

For example, $CY_1$ to $CY_4$ may be each independently selected from a pyrrole, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a benzimidazole, a benzoxazole, an iso-benzoxazole, a triazole, a tetrazole, an oxadiazole, a triazine, a pyridoindole, a pyridofuran, and a pyridothiophene.

According to an embodiment, $CY_1$ above may be selected from a pyridine, a pyrazine, a pyrimidine, a pyridazine, a quinoline, an isoquinoline, a benzoquinoline, a quinoxaline, a quinazoline, a pyridoindole, a pyridofuran, and a pyridothiophene.

According to another embodiment, $CY_2$ may be an imidazole or a pyrazolyl.

According to another embodiment, $CY_3$ and $CY_4$ may be each independently selected from a pyridine, a pyrazine, a pyrimidine, a pyridazine, a quinoline, an isoquinoline, a benzoquinoline, a quinoxaline, or a quinazoline.

$Z_1$ in $CY_1$ and $Z_2$ in $CY_2$ may optionally bind to each other through a single bond or a first linking group to form a saturated or an unsaturated ring, and the first linking group may be selected from linking groups represented by Formula 6 below:

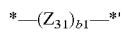

Formula 6

$Z_{31}$ in Formula 6 may be selected from *—O—*', *—S—*', *—N($Q_{41}$)—*', *—C($Q_{42}$)($Q_{43}$)—*', *—C($Q_{44}$)=C($Q_{45}$)—*', and

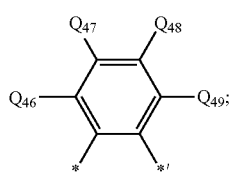

$Q_{41}$ to $Q_{49}$ may be each independently selected from a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group; and b1 may be an integer selected from 1 to 10 and when b1 is 2 or greater, groups $Z_{31}$ may be the same or different.

Descriptions of $Q_{41}$ to $Q_{49}$ may be understood by referring to the description of $Z_1$ herein.

In Formula 2A, $Y_1$ and $Y_2$ may be each independently C or N.

In Formulae 2C and 2D,
$X_1$ may be N or $CR_1$,
$X_2$ may be N or $CR_2$,
$X_3$ may be N or $CR_3$,
$X_4$ may be N or $CR_4$,
$X_{11}$ may be N or $CR_{11}$,
$X_{12}$ may be N or $CR_{12}$,
$X_{13}$ may be N or $CR_{13}$,
$X_{14}$ may be N or $CR_{14}$,
$X_{15}$ may be N or $CR_{15}$, and
$X_{16}$ may be N or $CR_{16}$.

According to an embodiment, in Formula 2C, at least one selected from $X_1$ to $X_4$ may be N.

In Formula 2E, $R_{21}$ and $R_{22}$ may optionally bind to each other by a single bond or via a second linking group represented by Formula 3.

$$*-(Z_{32})_{b2}-*' \qquad \text{Formula 3}$$

In Formula 3, $Z_{32}$ may be selected from *—O—', *—S—*', *—N($Q_{51}$)—*', *—C($Q_{52}$)($Q_{53}$)—*', *—C($Q_{54}$)=C($Q_{55}$)—*', and

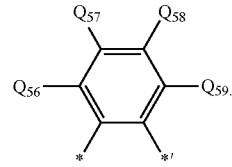

$R_{41}$ to $R_{47}$, $Z_1$ to $Z_6$, $R_1$ to $R_4$, $R_{11}$ to $R_{16}$, and $Q_{51}$ to $Q_{59}$ may be each independently selected from a hydrogen, a deuterium, —F (a fluoro group), —Cl (a chloro group), —Br (a bromo group), —I (an iodo group), a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$); and $R_{21}$ and $R_{22}$ may be each independently selected from a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed heteropolycyclic group.

According to an embodiment, the $R_{41}$ to $R_{47}$, $Z_1$ to $Z_6$, $R_1$ to $R_4$, $R_{11}$ to $R_{16}$, and $Q_51$ to $Q_{59}$ may be each independently selected from a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, —SF$_5$, a C$_1$-C$_{60}$ alkyl group, a C$_2$-C$_{60}$ alkenyl group, a C$_2$-C$_{60}$ alkynyl group, and a C$_1$-C$_{60}$ alkoxy group;

a C$_1$-C$_{60}$ alkyl group, a C$_2$-C$_{60}$ alkenyl group, a C$_2$-C$_{60}$ alkynyl group, and a C$_1$-C$_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a pyridinyl group, and a pyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_1$-C$_{60}$ alkyl group substituted with at least one —F, a C$_1$-C$_{60}$ alkoxy group substituted with at least one —F, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —N(Q$_{31}$)(Q$_{32}$), —Si(Q$_{33}$)(Q$_{34}$)(Q$_{35}$), and —B(Q$_{36}$)(Q$_{37}$); and —N(Q$_1$)(Q$_2$), —Si(Q$_3$)(Q$_4$)(Q$_5$), and —B(Q$_6$)(Q$_7$); wherein, Q$_1$ to Q$_7$ and Q$_{31}$ to Q$_{37}$ may be each independently selected from a hydrogen, a C$_1$-C$_{20}$ alkyl group, a C$_1$-C$_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

According to another embodiment, the R$_{41}$ to R$_{47}$, Z$_1$ to Z$_6$, R$_1$ to R$_4$, R$_{11}$ to R$_{16}$, and Q$_{51}$ to Q$_{59}$ may be each independently selected from a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, —SF$_5$, a C$_1$-C$_{20}$ alkyl group, and a C$_1$-C$_{20}$ alkoxy group;

a C$_1$-C$_{20}$ alkyl group and a C$_1$-C$_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a $C_1$-$C_{20}$ alkyl group substituted with at least one —F, a $C_1$-$C_{20}$ alkoxy group substituted with at least one —F, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group.

According to another embodiment, the $R_{41}$ to $R_{47}$, $Z_1$ to $Z_6$, $R_1$ to $R_4$, $R_{11}$ to $R_{16}$, and $Q_{51}$ to $Q_{59}$ may be each independently selected from a hydrogen, —F, a cyano group, a nitro group, —SF$_5$, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group and a triazinyl group; and a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, or a triazinyl group, each substituted with at least one selected from —F, a cyano group, and a nitro group, but they are not limited thereto.

In Formula 2E, the following conditions regarding $R_{21}$ and $R_{22}$ are excluded:

i) where $R_{21}$ and $R_{22}$ are both phenyl groups, ii) where $R_{21}$ and $R_{22}$ are both phenyl groups substituted with a tert-butyl group, iii) where $R_{21}$ and $R_{22}$ are both ethyl groups, iv) where $R_{21}$ and $R_{22}$ are both propyl groups, v) where $R_{21}$ and $R_{22}$ are both butyl groups, and vi) where $R_{21}$ and $R_{22}$ are both —Si(CH$_3$)$_3$.

According to an embodiment, in Formula 2E, cases in which i) $R_{21}$ and $R_{22}$ are not connected to each other and $R_{21}$ and $R_{22}$ are phenyl groups, and ii) $R_{21}$ and $R_{22}$ are not connected to each other and $R_{21}$ and $R_{22}$ are phenyl groups substituted with one $C_1$-$C_{60}$ alkyl group may be excluded; and cases in which i) $R_{21}$ and $R_{22}$ are connected by a single bond or via a second linking group, wherein the second linking group is *—O—*' or *—S—*' and all of $R_{21}$ and $R_{22}$ are phenyl groups, and ii) $R_{21}$ and $R_{22}$ are connected by a single bond or via a second linking group, wherein the second linking group is *—O—*' or *—S—*', and all of $R_{21}$ and $R_{22}$ are substituted with one $C_1$-$C_{60}$ alkyl group may be excluded.

According to another embodiment, in Formula 1, at least one selected from $R_{45}$ and $R_{46}$ may not be a hydrogen.

According to another embodiment, in Formula 1, $R_{45}$ and $R_{46}$ may be different.

According to another embodiment, in Formula 1, at least one selected from $R_{45}$ and $R_{46}$ may be —F, a cyano group, or —CF$_3$, but it is not limited thereto.

In Formula 1, both $R_{45}$ and $R_{46}$ are not —F.

In Formula 1, when $L_1$ includes the second ligand or the third ligand, each of $R_{41}$ to $R_{47}$ is not a hydrogen.

In Formula 2D, at least one selected from $X_{11}$ to $X_{16}$ is N.

In Formula 2A, a1 represents the number of groups $Z_1$ and may be an integer selected from 1 to 5. For example, a1 may be 1, 2, or 3, but it is not limited thereto. When a1 is 2 or greater, two or more groups $Z_1$ may be the same or different. Each of a2 to a4 represents the number of groups $Z_2$ to $Z_4$, and descriptions thereof may be understood by referring to the description of a1.

In Formula 1, n1 may be an integer selected from 0 to 2 and n2 may be an integer selected from 1 to 3. When n1 is 0, $L_1$ is absent in Formula 1.

According to an embodiment, in Formula 1, n1 may be 0 or 1.

In Formula 2A, a bond between N and $Y_1$ and a bond between N and $Y_2$, and in Formula 2B, a bond between C and N may be each independently a single bond or a double bond.

According to an embodiment, the first ligand may be represented by any one selected from Formulae 2A-1 to 2A-45:

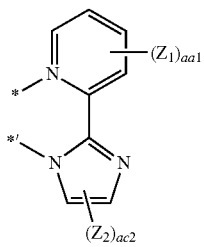

Formula 2A-1

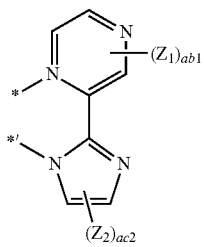

Formula 2A-2

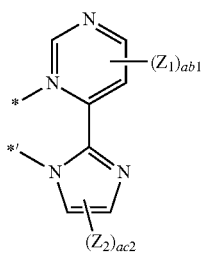

Formula 2A-3

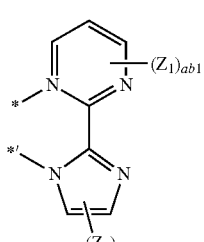

Formula 2A-4

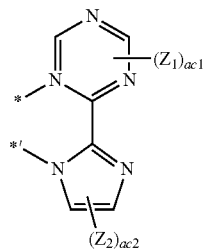

Formula 2A-5

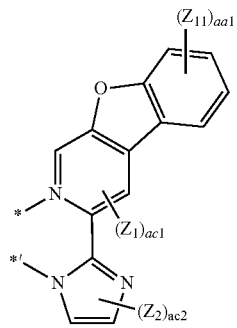

Formula 2A-6

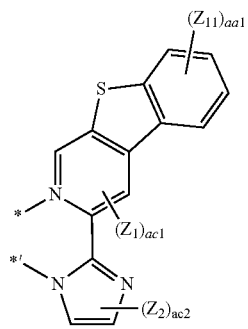

Formula 2A-7

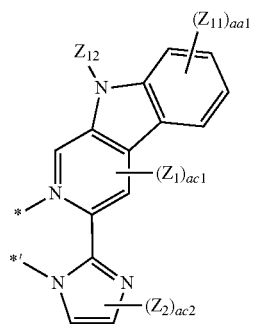

Formula 2A-8

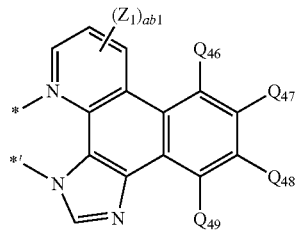

Formula 2A-9

Formula 2A-10
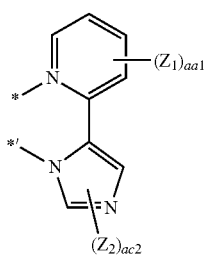
Formula 2A-11
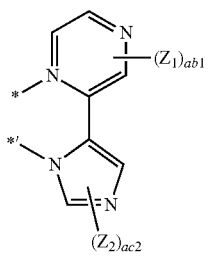
Formula 2A-12
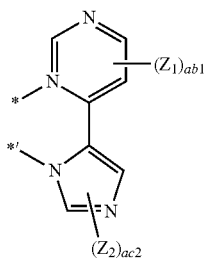
Formula 2A-13
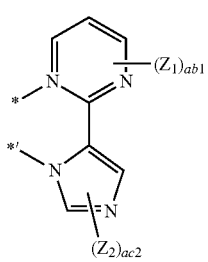
Formula 2A-14
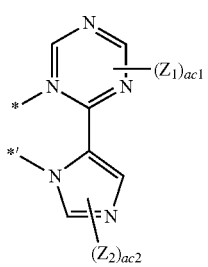
Formula 2A-15
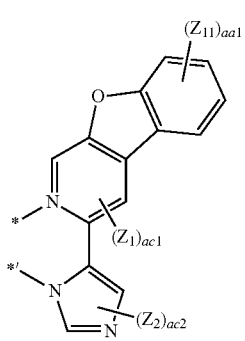
Formula 2A-16
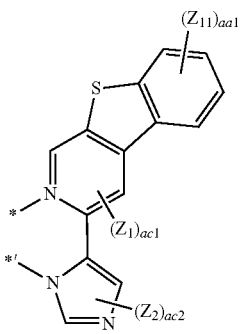
Formula 2A-17
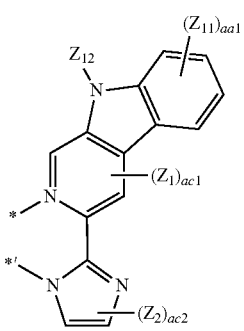
Formula 2A-18
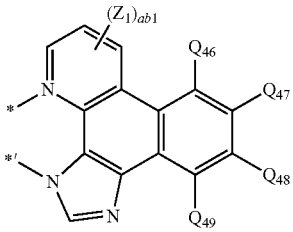
Formula 2A-19
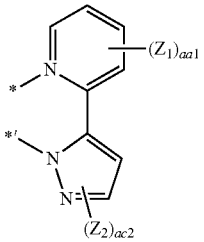
Formula 2A-20
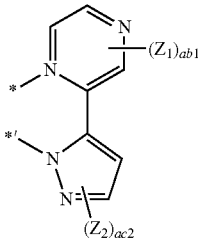

Formula 2A-21
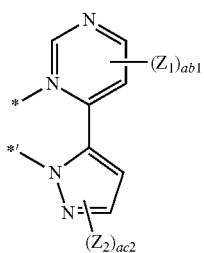
Formula 2A-22
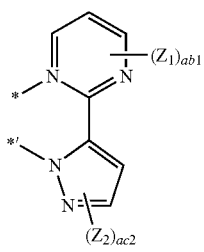
Formula 2A-23
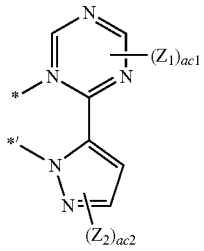
Formula 2A-24
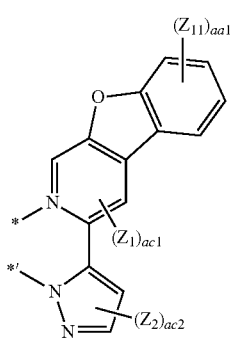
Formula 2A-25
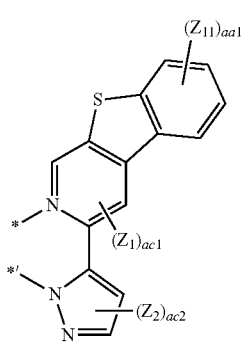
Formula 2A-26
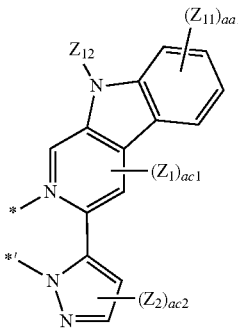
Formula 2A-27
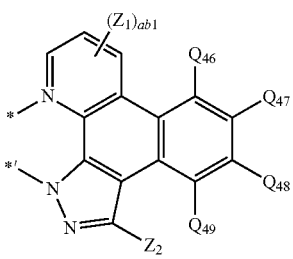
Formula 2A-28
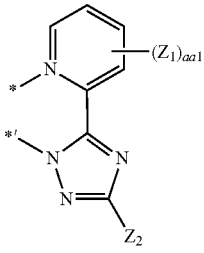
Formula 2A-29
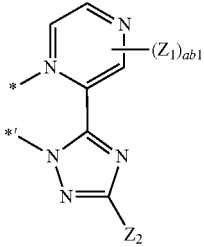
Formula 2A-30
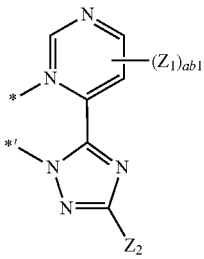
Formula 2A-31
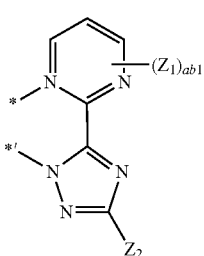

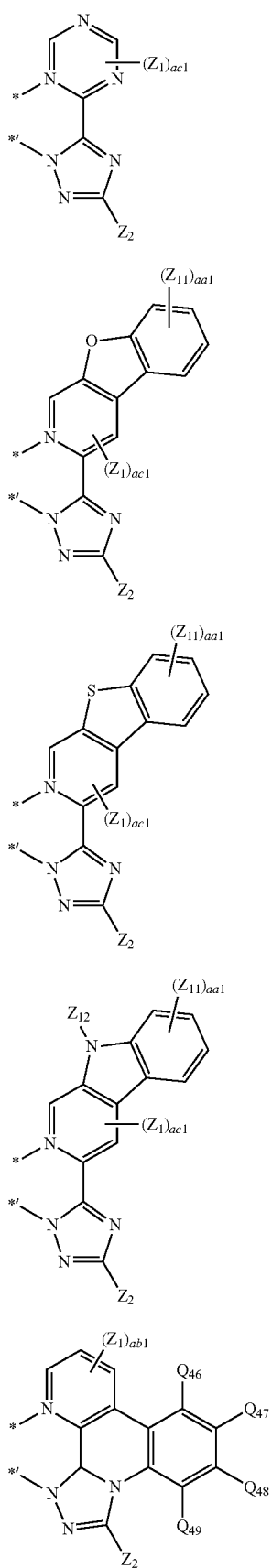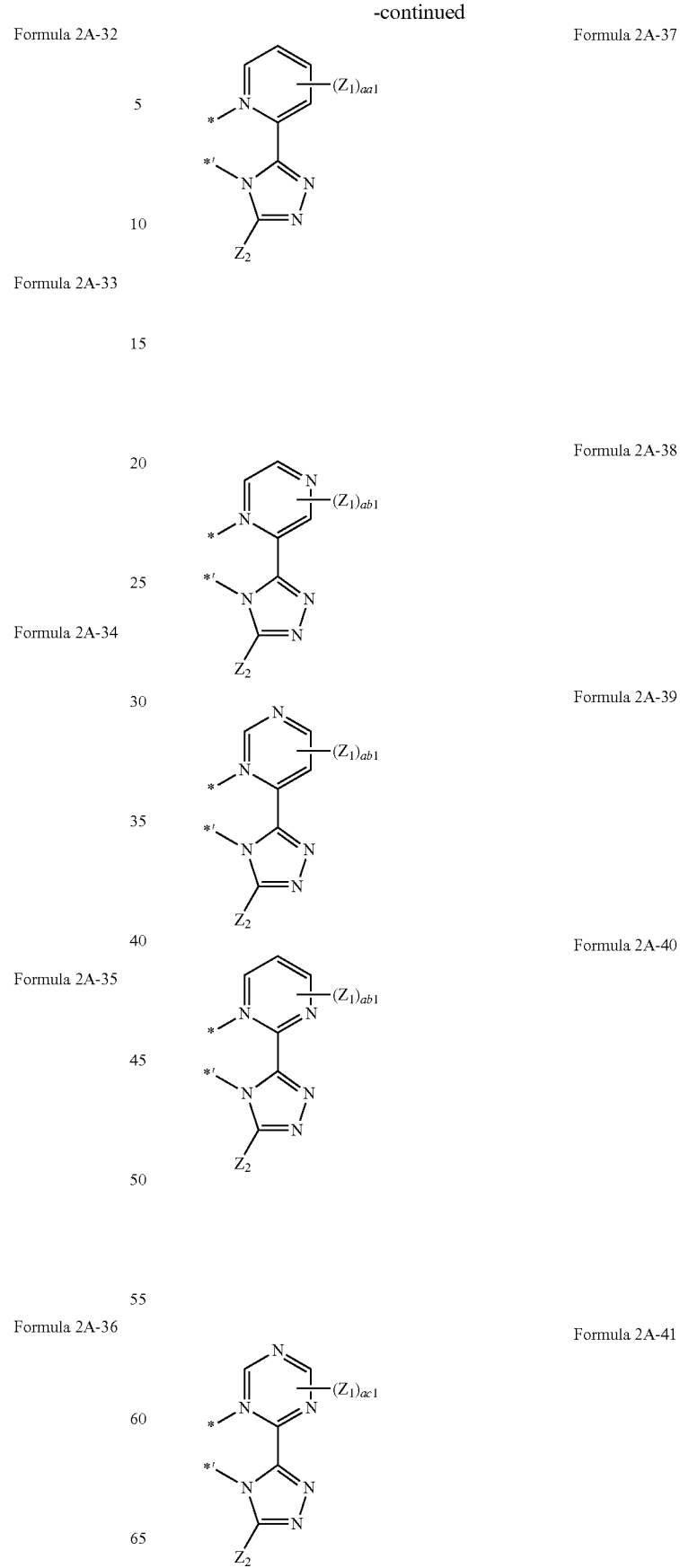

-continued

Formula 2A-42
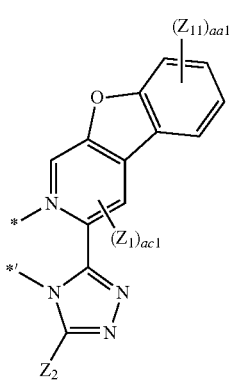

Formula 2A-43
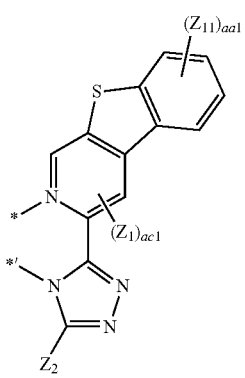

Formula 2A-44
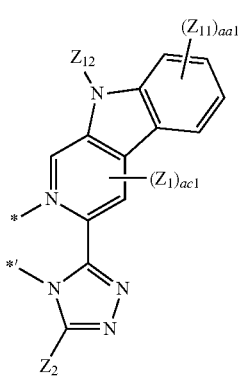

Formula 2A-45
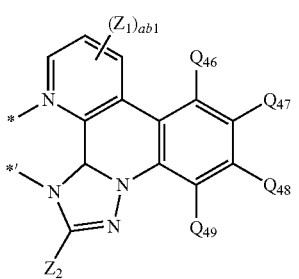

In Formulae 2A-1 to 2A-45,
$Z_1$, $Z_2$, $Z_{11}$ to $Z_{13}$, and $Q_{46}$ to $Q_{49}$ may be understood by descriptions herein,
aa1 may be an integer selected from 1 to 4,
ab1 and ab2 may be each independently integers selected from 1 to 3, and
ac1 and ac2 may be each independently 1 or 2.
According to another embodiment, the second ligand may be represented by any one selected from Formula 2B-1 to 2B-25:

Formula 2B-1
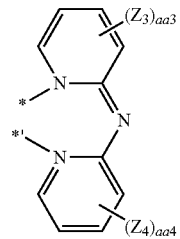

Formula 2B-2
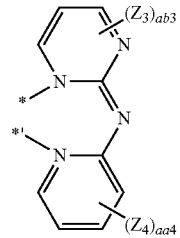

Formula 2B-3
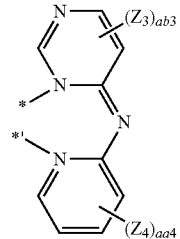

Formula 2B-4
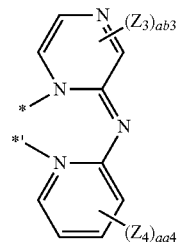

Formula 2B-5
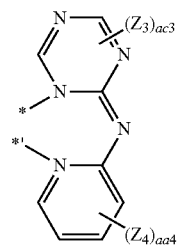

Formula 2B-6
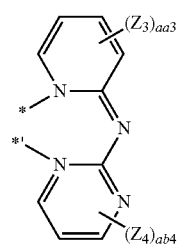

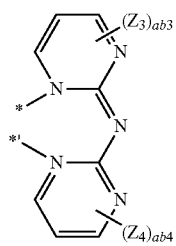
Formula 2B-7
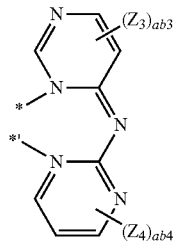
Formula 2B-8
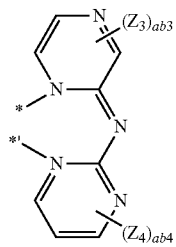
Formula 2B-9
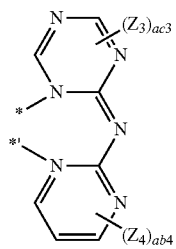
Formula 2B-10
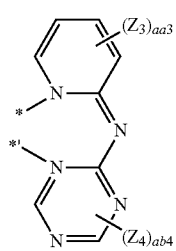
Formula 2B-11
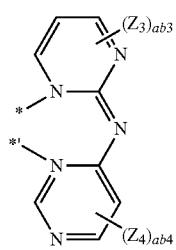
Formula 2B-12
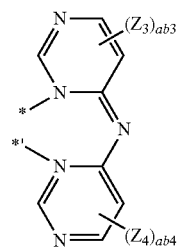
Formula 2B-13
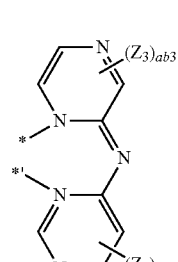
Formula 2B-14
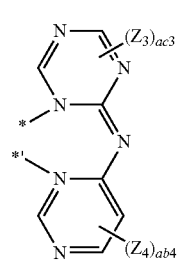
Formula 2B-15
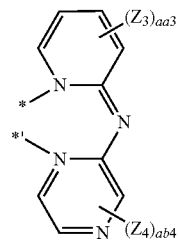
Formula 2B-16
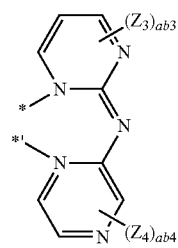
Formula 2B-17
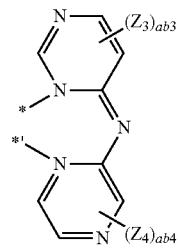
Formula 2B-18

-continued

Formula 2B-19 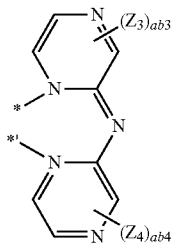

Formula 2B-20 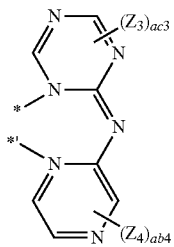

Formula 2B-21 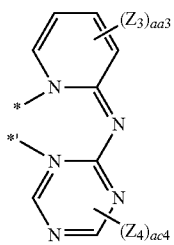

Formula 2B-22 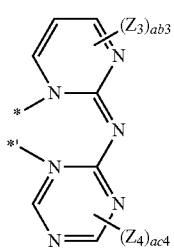

Formula 2B-23 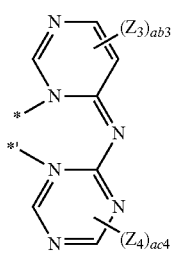

Formula 2B-24 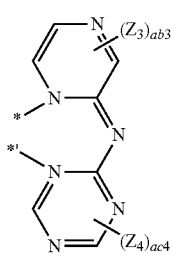

Formula 2B-25 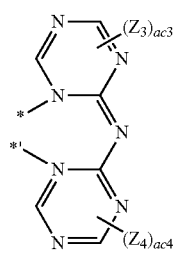

In Formulae 2B-1 to 2B-25, descriptions of $Z_3$ and $Z_4$ may be understood by referring to the descriptions herein, and aa3 and aa4 may be each independently integers selected from 1 to 4, ab3 and ab4 may be each independently integers selected from 1 to 3, ac3 and ab4 may be each independently 1 or 2, and

* and *' are binding sites to M in Formula 1.

According to another embodiment, the third ligand may be represented by any one selected from Formulae 2C-1 to 2C-4 and 2D-1 to 2D-4:

Formula 2C-1 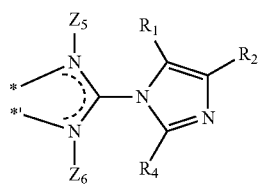

Formula 2C-2 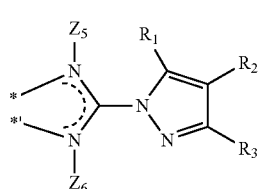

Formula 2C-3 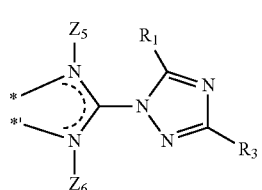

Formula 2C-4 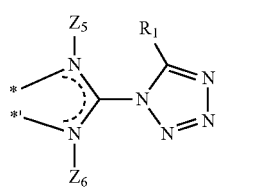

-continued

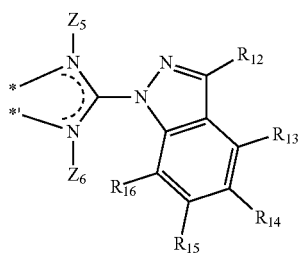

Formula 2D-1

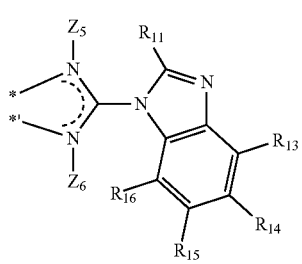

Formula 2D-2

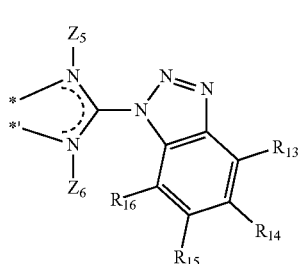

Formula 2D-3

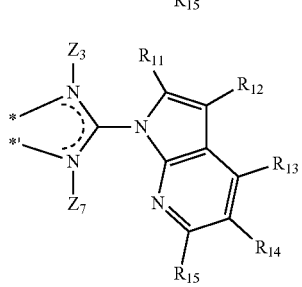

Formula 2D-4

In Formulae 2C-1 to 2C-4 and 2D-1 to 2D-4, descriptions of $Z_5$, $Z_6$, $R_1$ to $R_4$, and $R_{11}$ to $R_{16}$ may be understood by referring to the descriptions herein.

For example, in Formulae 2A-1 to 2A-45, 2B-1 to 2B-25, 2C-1 to 2C-4, and 2D-1 to 2D-4, $Z_1$ to $Z_6$, $Z_{11}$ to $Z_{13}$, $R_1$ to $R_4$, $R_{11}$ to $R_{16}$, and $Q_{46}$ to $Q_{49}$ may be each independently selected from a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; but they are not limited thereto.

In Formula 2E, $R_{21}$ and $R_{22}$ may be each independently selected from a cyano group;

a $C_1$-$C_{20}$ alkyl group substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a pyridinyl group, and a pyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzoiuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

the $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

at least one selected from $R_{21}$ and $R_{22}$ may be selected from a cyano group;

a $C_1$-$C_{20}$ alkyl group substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a pyridinyl group, and a pyrimidinyl group;

a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyhdinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluoronyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group.

For example, in Formula 2E, $R_{21}$ and $R_{22}$ may be each independently selected from a cyano group;

a phenyl group, a naphthyl group, a fluorenyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a triazinyl group, a dibenzofuranyl group, and a dibenzothiophenyl group; and a phenyl group, a naphthyl group, a fluorenyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, a fluorenyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a triazinyl group, a dibenzofuranyl group, and a dibenzothiophenyl group;

at least one selected from $R_{21}$ and $R_{22}$ may be selected from a cyano group;

a naphthyl group, a fluorenyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a triazinyl group, a dibenzofuranyl group, and a dibenzothiophenyl group; and a naphthyl group, a fluorenyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, a fluorenyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a triazinyl group, a dibenzofuranyl group, and a dibenzothiophenyl group.

According to an embodiment, the third ligand may be selected from Formula 2E(1) or 2E(2):

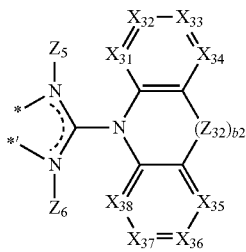

Formula 2E(1)

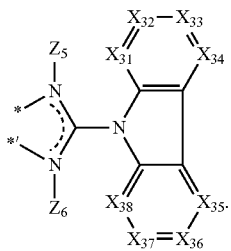

Formula 2E(2)

In Formulae 2E(1) and 2E(2), descriptions of $Z_5$, $Z_6$, $Z_{32}$, and b2 may be understood by referring to the descriptions herein;

$X_{31}$ may be N or $CR_{31}$, $X_{32}$ may be N or $CR_{32}$, $X_{33}$ may be N or $CR_{33}$, $X_{34}$ may be N or $CR_{34}$, $X_{35}$ may be N or $CR_{35}$, $X_{36}$ may be N or $CR_{36}$, $X_{37}$ may be N or $CR_{37}$, $X_{38}$ may be N or $CR_{38}$, and at least one selected from $X_{31}$ to $X_{38}$ may be N; and descriptions of $R_{31}$ to $R_{38}$ may be each independently the same as the description for $R_1$.

According to another embodiment, the third ligand may be represented by any one selected from Formulae 2E-1 to 2E-25:

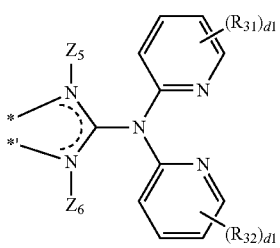

Formula 2E-1

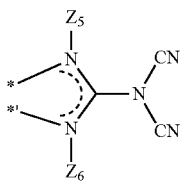

Formula 2E-2

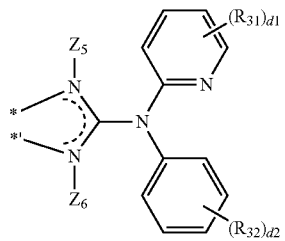

Formula 2E-3

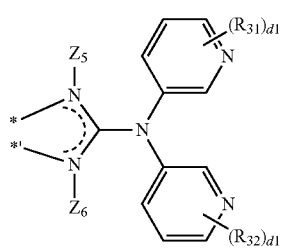

Formula 2E-4

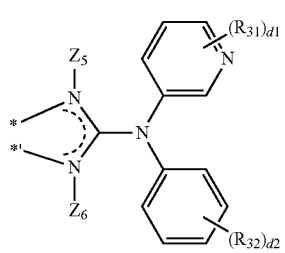

Formula 2E-5

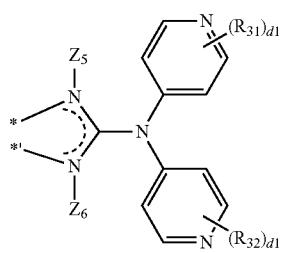

Formula 2E-6

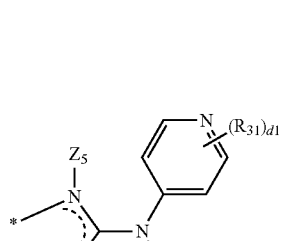

Formula 2E-7

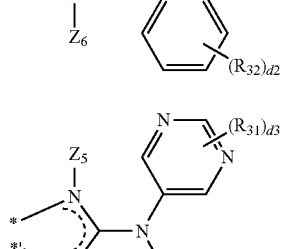

Formula 2E-8

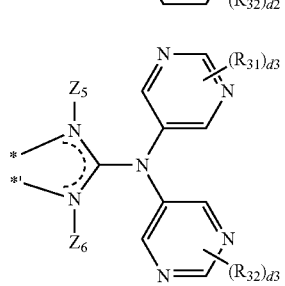

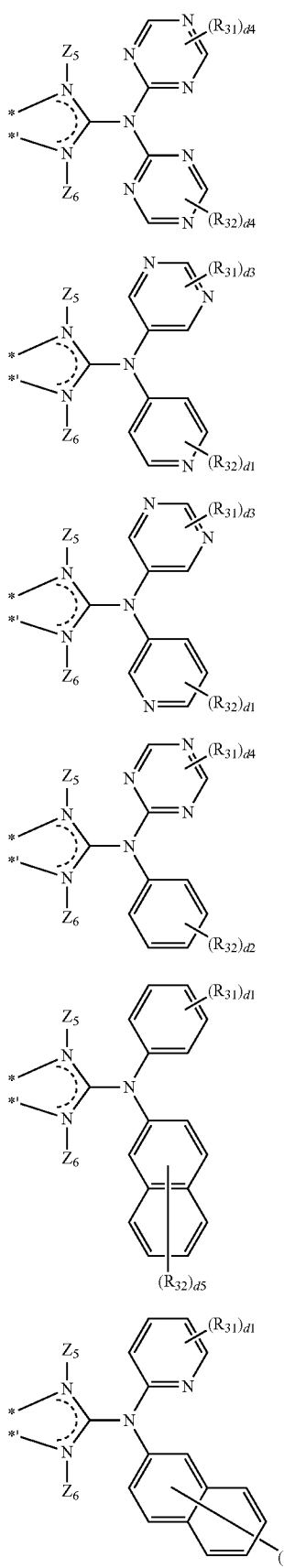
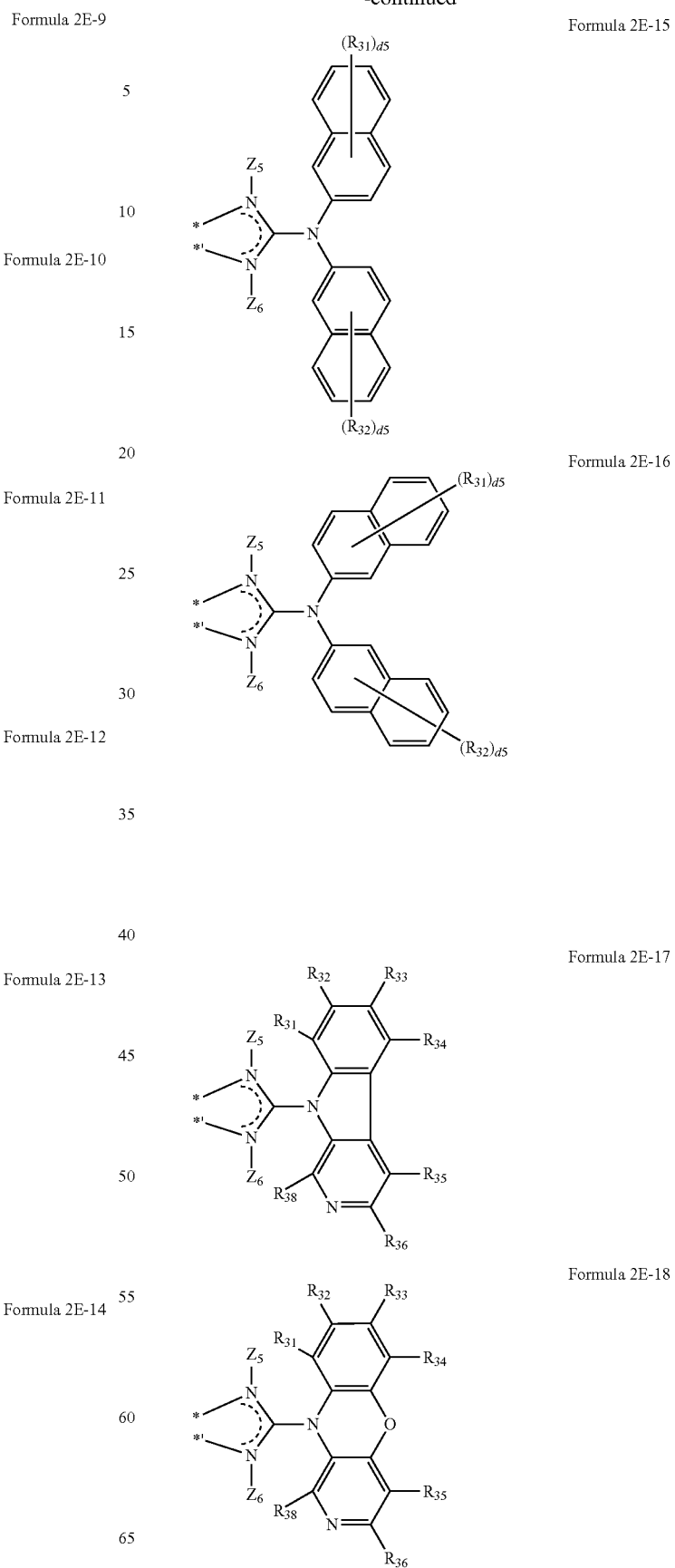

-continued

Formula 2E-19
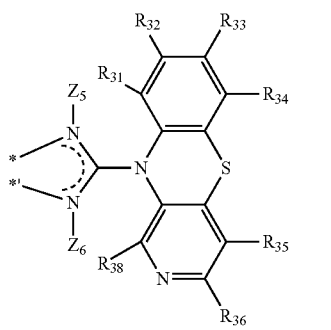

Formula 2E-20
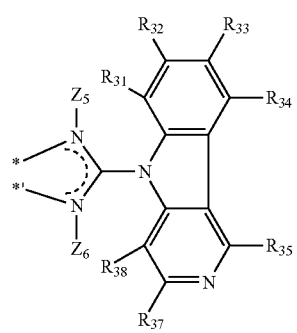

Formula 2E-21
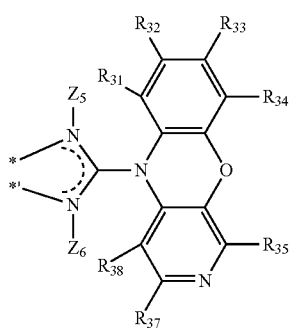

Formula 2E-22
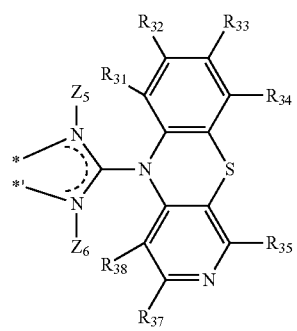

Formula 2E-23
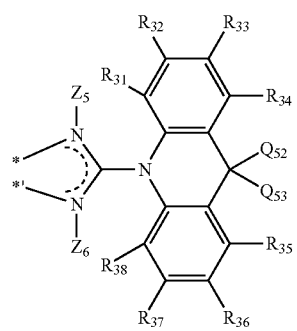

Formula 2E-24
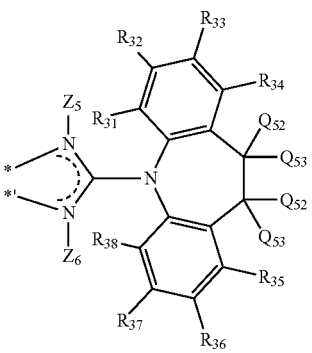

Formula 2E-25
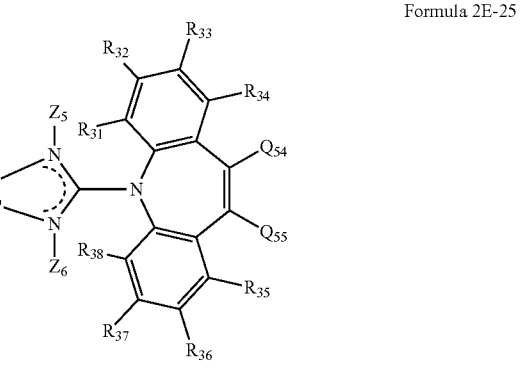

In Formulae 2E-1 to 2E-25, descriptions of $Z_5$, $Z_6$, $R_{31}$ to $R_{38}$, and $Q_{52}$ to $Q_{55}$ may be understood by referring to the description herein, d1 may be an integer selected from 1 to 4, d2 may be an integer selected from 1 to 5, d3 may be an integer selected from 1 to 3, d4 may be 1 or 2, and d5 may be an integer selected from 1 to 7.

For example, in Formulae 2E-1 to 2E-25, $Z_5$, $Z_6$, $R_{31}$ to $R_{38}$, and $Q_{52}$ to $Q_{55}$ may be each independently selected from a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —N($Q_1$)($Q_2$), —Si($Q_3$)($Q_4$)($Q_5$), and —B($Q_6$)($Q_7$), wherein;

$Q_1$ to $Q_7$ may be each independently selected from a hydrogen, a $C_1$-$C_{20}$ alkyl group, a $C_1$-$C_{20}$ alkoxy group, a phenyl group, and a naphthyl group, but they are not limited thereto.

According to an embodiment, the organometallic compound may be represented by Formula 1A below:

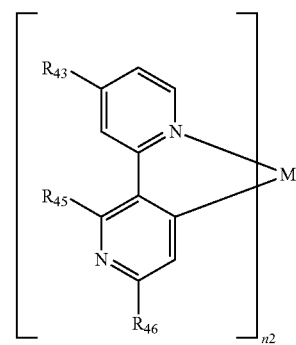

Formula 1A

In Formula 1A, descriptions of $R_{43}$, $R_{45}$, $R_{46}$, M, and n2 may be understood by referring to the descriptions herein.

For example, in Formula 1A, $R_{43}$, $R_{45}$, and $R_{46}$ may be each independently selected from a hydrogen, —F, a cyano group, a nitro group, —$SF_5$, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group and a triazinyl group; and a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group, each substituted with at least one selected from —F, a cyano group, and a nitro group; wherein cases in which both $R_{45}$ and $R_{46}$ are not —F;

both $R_{45}$ and $R_{46}$ are not a hydrogen; and n2 may be 2 or 3, but they are not limited thereto.

According to another embodiment, in Formula 1 above, n1 is 1 or 2;

$L_1$ may be a ligand represented by Formula 2A-19, a ligand represented by Formula 2B-1, and a ligand represented by Formula 2E-17, but it is not limited thereto:

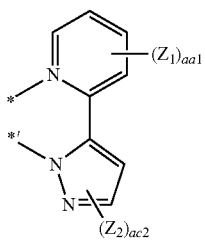

Formula 2A-19

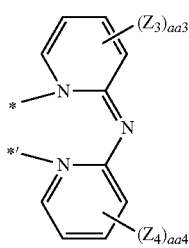

Formula 2B-1

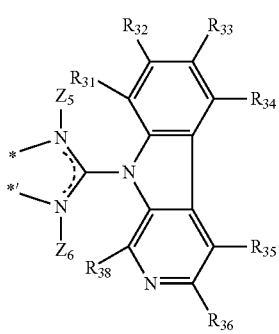

Formula 2E-17

In Formulae 2A-19, 2B-1, and 2E-17, $Z_1$ to $Z_6$, $R_{31}$ to $R_{36}$, and $R_{38}$ may be each independently selected from a hydrogen, —F, a cyano group, a nitro group, —SF$_5$, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group; and a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group, each substituted with at least one selected from —F, a cyano group, and a nitro group, and aa1, aa3, aa4, and ac2 may be each independently 1 or 2.

The organometallic compound represented by Formula 1 may be any one selected from Compounds 1 to 22.

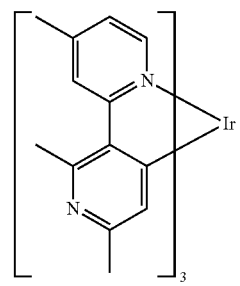

1

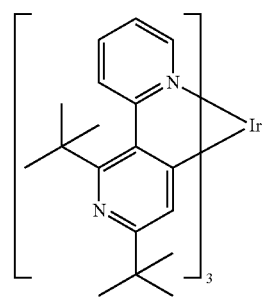

2

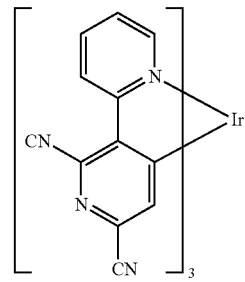

3

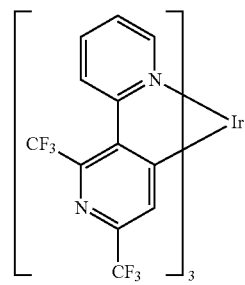

4

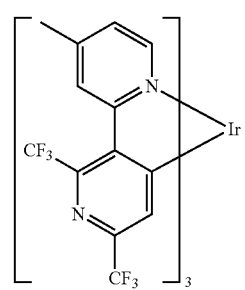

5

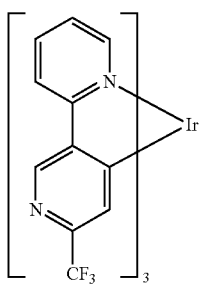
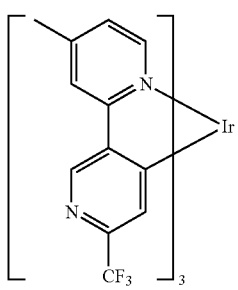
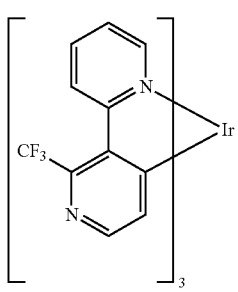
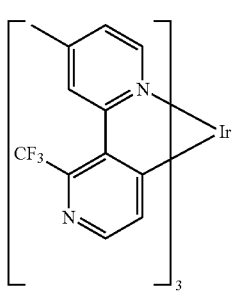
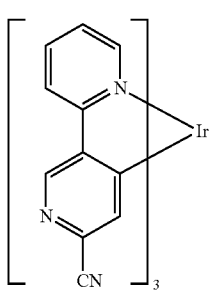
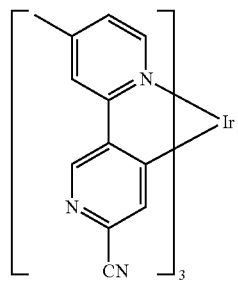
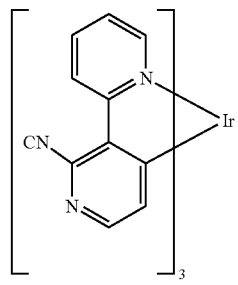
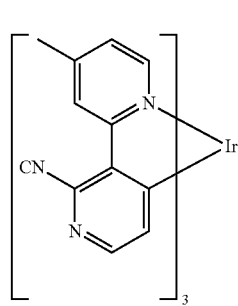
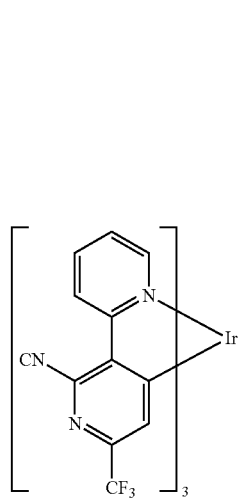
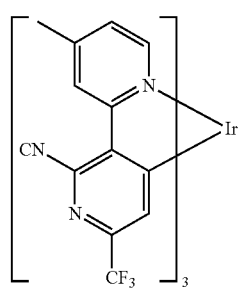

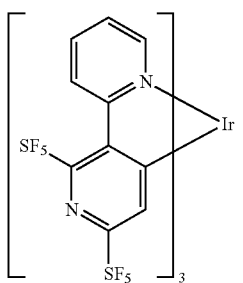

16

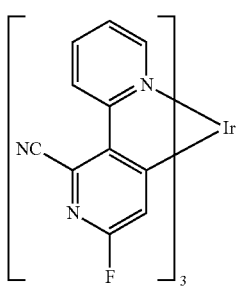

17

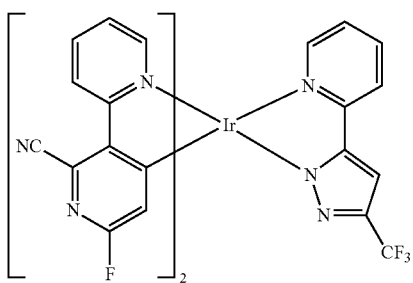

18

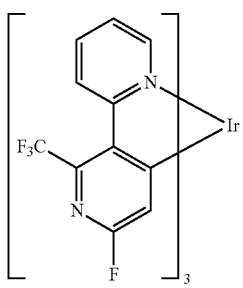

19

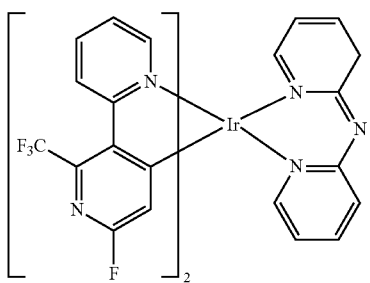

20

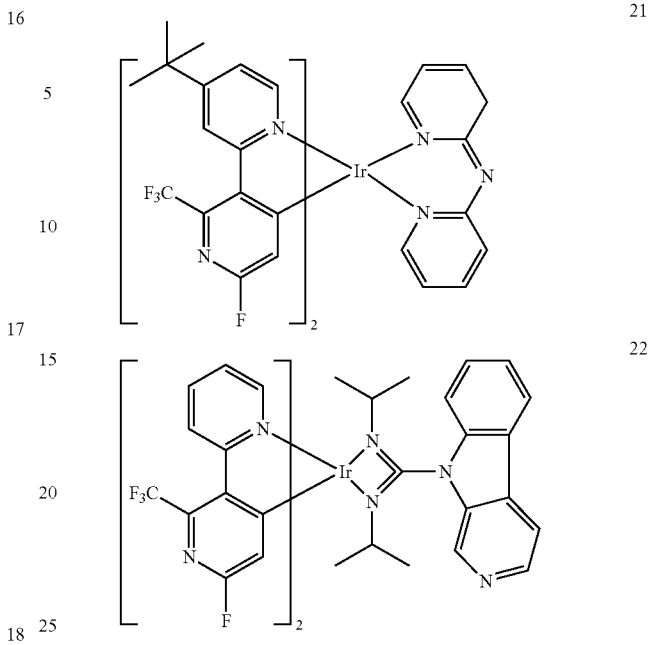

21

22

Since the organometallic compound represented by Formula 1 above includes Ligand 1 described as follows, the organometallic compound represented by Formula 1 capable of emitting deep blue light.

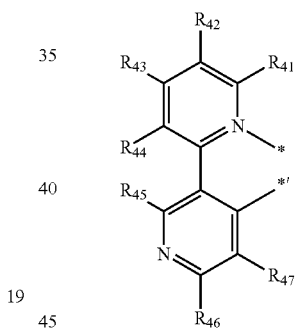

Ligand 1

In Formula 1, both $R_{45}$ and $R_{46}$ is not —F. While not wishing to be bound by theory, it is believed that, in Formula 1, when the organometallic compound in which both $R_{45}$ and $R_{46}$ are —F is used in an organic light-emitting device, —F may be dissociated from the organometallic compound to form F⁻ during an operation of the organic light-emitting device. Since F⁻ is highly reactive, dissociation of F⁻ may cause a decrease in the lifespan of the organic light-emitting device.

However, in Formula 1, the organic light-emitting device including an organometallic compound, in which both $R_{45}$ and $R_{46}$ are not —F, may emit deep blue light having excellent color coordination and may have a long lifespan.

In Formula 2E defined according to the description above, $R_{21}$ and $R_{22}$ may not be an "unsubstituted $C_1$-$C_{60}$ alkyl group". As a result, an organometallic compound including a third ligand represented by Formula 2E may have excellent dispersibility to prevent the aggregation of molecules, and thus, an organic light-emitting device including the organometallic compound may have high efficiency and a long lifespan due to improvement in charge mobility.

The preparation of the organometallic compound represented by Formula 1 above may be understood by one of ordinary skill in the art with reference to Synthesis Examples described below.

Accordingly, the organometallic compound represented by Formula 1 above may be used as an organic layer of an organic light-emitting device, for example, as a dopant in an emission layer (EML) of the organic layer. According to another embodiment, provided is an organic light-emitting device including a first electrode;

a second electrode; and an organic layer disposed between the first electrode and the second electrode, wherein the organic layer includes an EML and at least one organometallic compound represented by Formula 1 above.

The organic light-emitting device may include the organic layer including the organometallic compound represented by Formula 1 to have a low driving voltage, high efficiency, high brightness, and a long lifespan. Also, the organic light-emitting device including the organometallic compound represented by Formula 1 above is capable of emitting blue light having a maximum emission wavelength in a range of about 440 nanometers (nm) to about 500 nm, an x color coordinate in a range of about 0.16 to about 0.22, and a y color coordinate in a range of about 0.10 to about 0.40.

The organometallic compound represented by Formula 1 above may be used between a pair of electrodes in an organic light-emitting device. For example, the organometallic compound represented by Formula 1 above may be included therein. In this regard, the organometallic compound acts as a dopant and the EML may further include a host (in other words, the amount of the organometallic compound represented by Formula 1 above may be smaller than the amount of the host).

As used herein, the expression the "(organic layer) includes at least one organometallic compound" may be construed as meaning the "(organic layer) may include one organometallic compound within the scope of Formula 1 or two different organometallic compounds within the scope of Formula 1".

For example, the organic layer may include only Compound 1 as the organometallic compound. In this regard, Compound 1 may be included in the EML of the organic light-emitting device. Alternatively, the organic layer may include Compound 1 and Compound 2 as the organometallic compounds. In this regard, Compound 1 and Compound 2 may be included in the same layer (for example, Compound 1 and Compound 2 may both be included in the EML).

The first electrode may be an anode, which is a hole injection electrode, and the second electrode may be a cathode, which is an electron injection electrode. Alternatively, the first electrode may be a cathode, which is an electron injection electrode, and the second electrode may be an anode, which is a hole injection electrode.

For example, the first electrode may be an anode, the second electrode may be a cathode, and the organic layer may include i) a hole transport region disposed between the first electrode and the EML, wherein the hole transport region may include at least one selected from a hole injection layer, a hole transport layer, and an electron blocking layer; and ii) an electron transport region disposed between the EML and the second electrode, wherein the electron transport region may include at least one selected from a hole blocking layer (HBL), an electron transport layer, and an electron injection layer.

As used herein, the term "organic layer" refers to a single and/or a plurality of layers disposed between the first electrode and the second electrode in an organic light-emitting device. The "organic layer" may include not only organic compounds but also organometallic complexes including metals.

The FIGURE is a schematic view of an organic light-emitting device 10 according to an embodiment. Hereinafter, a structure and a method of manufacturing an organic light-emitting device, according to an embodiment, will be described with reference to the FIGURE. The organic light-emitting device 10 includes a first electrode 11, an organic layer 15, and a second electrode 19, which are sequentially layered in the stated order.

A substrate may be additionally disposed under the first electrode 11 or on the second electrode 19. The substrate may be a conventional glass substrate or a transparent plastic substrate, each having excellent mechanical strength, thermal stability, transparency, surface smoothness, ease of handling, and water repellency.

The first electrode 11 may be formed by depositing or sputtering a material for forming the first electrode 11 on the substrate. The first electrode 11 may be an anode. The material for the first electrode 11 may be selected from materials with a high work function for easy hole injection. The first electrode 11 may be a reflective electrode, a semi-transmissive electrode, or a transmissive electrode. The material for the first electrode 110 may be selected from indium (In) tin (Sn) oxide (ITO), indium (In) zinc (Zn) oxide (IZO), tin (Sn) oxide ($SnO_2$), and zinc (Zn) oxide (ZnO). Alternatively, a metal such as magnesium (Mg), aluminum (Al), aluminum(Al)—lithium(Li) (Al—Li), calcium (Ca), magnesium (Mg)—indium (In) (Mg—In), and magnesium (Mg)—silver (Ag) (Mg—Ag).

The first electrode 11 may have a single layer structure or a multi-layer structure including two or more layers. For example, the first electrode 11 may have a triple-layer structure of ITO/Ag/ITO, but it is not limited thereto.

The organic layer 15 may be disposed on the first electrode 11.

The organic layer 15 may include a hole transport region, an EML, and an electron transport region.

The hole transport region may be disposed between the first electrode 11 and the EML.

The hole transport region may include at least one selected from a hole injection layer (HIL), a hole transport layer (HTL), an electron-blocking layer (EBL), and a buffer layer.

The hole transport region may only include an HIL or a HTL. Alternatively, the hole transport region may include a structure in which HIL/HTL or HIL/HTL/EBL are sequentially layered on the first electrode 11.

When the hole transport region includes the HIL, the HIL may be formed on the first electrode 11 by using various methods such as vacuum deposition, spin coating, casting, and a Langmuir-Blodgett (LB) method.

When an HIL is formed by vacuum deposition, for example, the vacuum deposition may be performed at a deposition temperature of about 100 to about 500° C., at a vacuum degree of about $10^{-8}$ to about $10^{-3}$ torr, and at a deposition rate of about 0.01 Angstroms per second (Å/sec) to about 100 Å/sec, though the conditions may vary depending on a compound that is used as a hole injection material and a structure and thermal properties of a desired HIL.

When an HIL is formed by spin coating, the spin coating may be performed at a coating rate of about 2,000 revolutions per minute (rpm) to about 5,000 rpm, and at a temperature of about 80° C. to 200° C. for removing a solvent after the spin coating, though the conditions may vary depending on a compound that is used as a hole injection material and a structure and thermal properties of a desired HIL.

The conditions for forming the HTL and EBL may be inferred based on the conditions for forming the HIL.

The hole transport region may include at least one selected from m-MTDATA, TDATA, 2-TNATA, NPB, β-NPB, TPD, a spiro-TPD, a spiro-NPB, α-NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

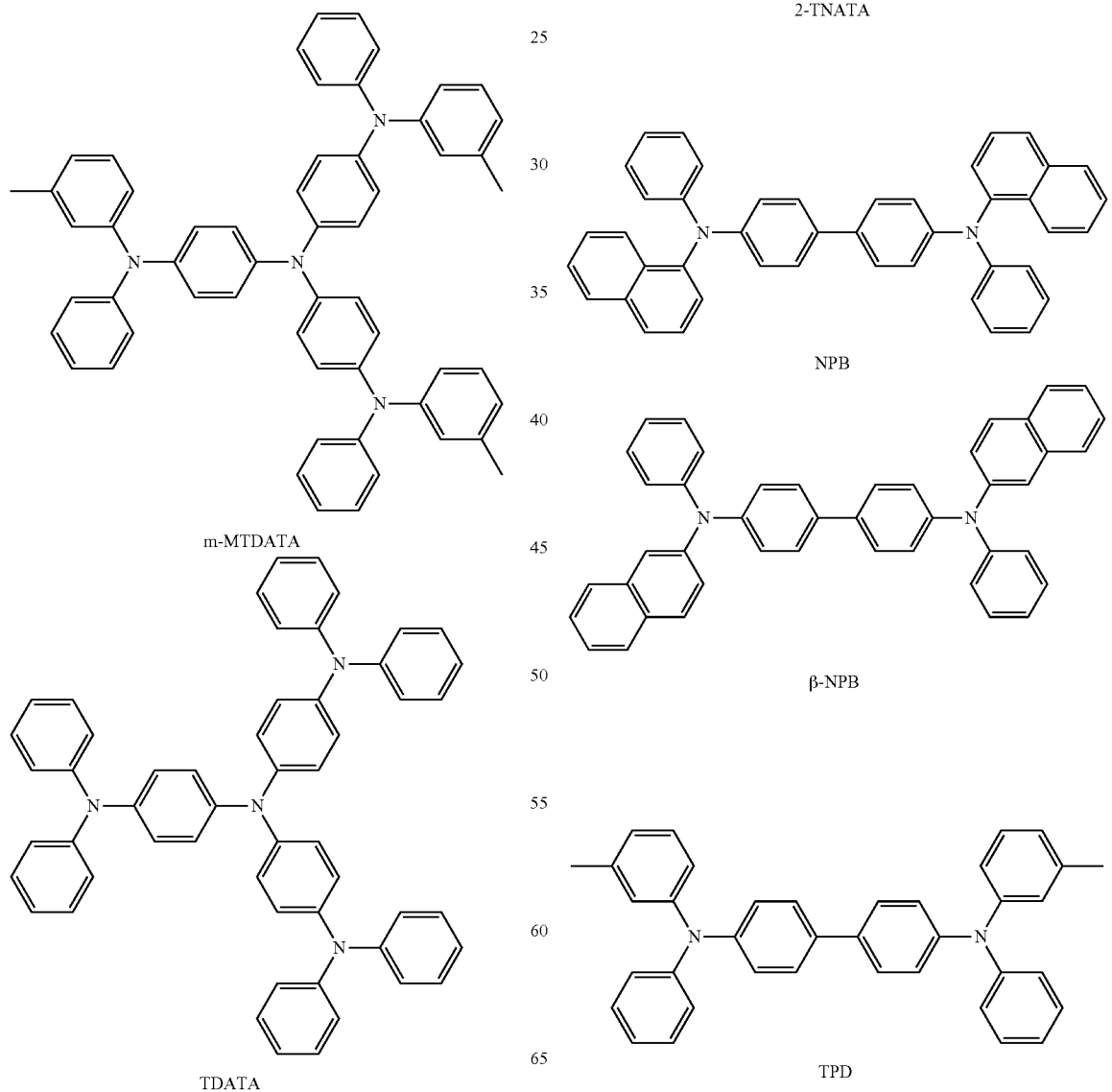

-continued
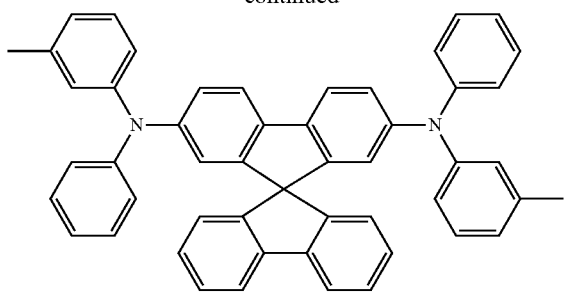
Spiro-TPD
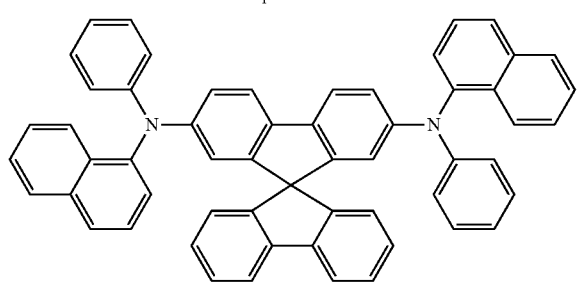
Spiro-NPB
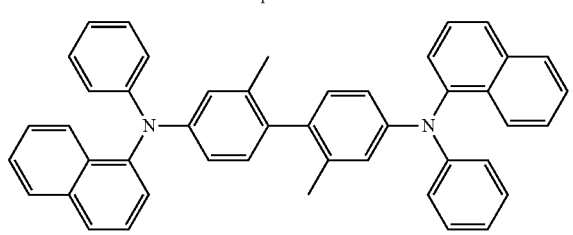
α-NPB
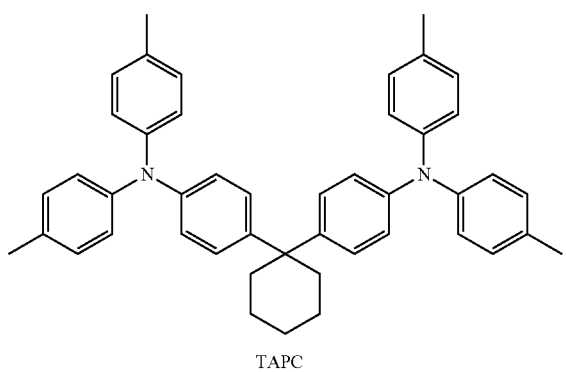
TAPC
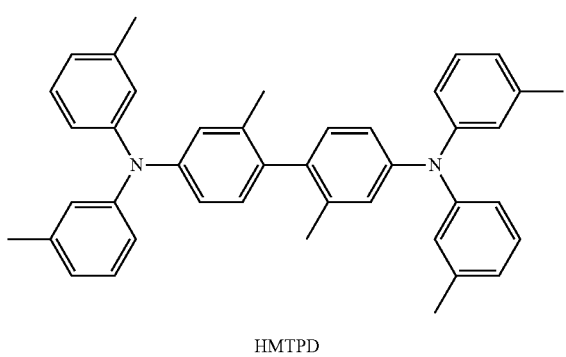
HMTPD
-continued
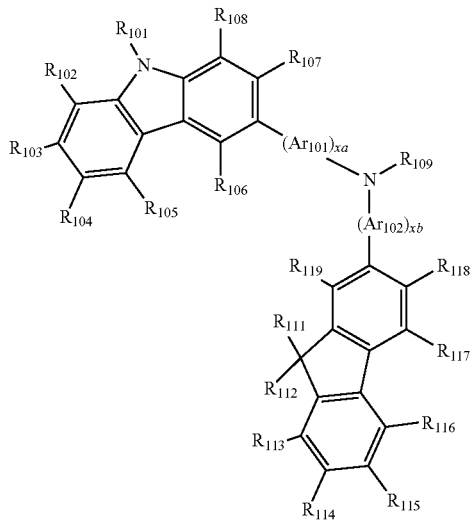
Formula 201
Formula 202

In Formula 201, $Ar_{101}$ and $Ar_{102}$ may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenyl group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenyl group, a pyrenylene group, a chrysenylenylene group, a naphthacenylene group, a picenylene group, a perylenylene group, and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

In Formula 201, xa and xb may be each independently an integer from 0 to 5, or 0, 1, or 2. For example, xa may be 1 and xb may be 0, but they are not limited thereto.

In Formulae 201 and 202, $R_{101}$ to $R_{108}$, $R_{111}$ to $R_{119}$, and $R_{121}$ to $R_{124}$ may be each independently one of a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, and a hexyl group), and a $C_1$-$C_{10}$ alkoxy group (for example, a methoxy group, an ethoxy group, a propoxy group, a butoxy group, and a pentoxy group);

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but they are not limited thereto.

In Formula 201, $R_{109}$ may be selected from a phenyl group, a naphthyl group, an anthracenyl group, and a pyridinyl group; and a phenyl group, a naphthyl group, an anthracenyl group, and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group.

According to an embodiment, the compound represented by Formula 201 may be represented by Formula 201A, but it is not limited thereto:

Formula 201A

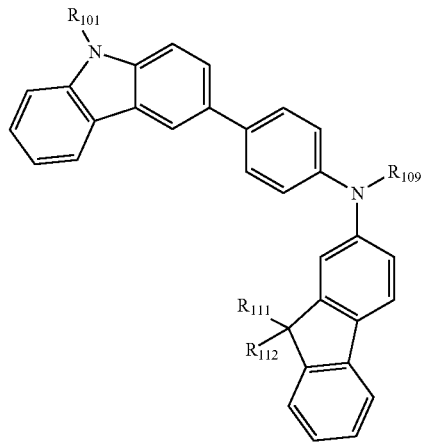

In Formula 201A, descriptions of $R_{101}$, $R_{111}$, $R_{112}$, and $R_{109}$ may be as described above.

For example, the compound represented by Formula 201 and the compound represented by Formula 202 may include Compounds HT1 to HT20, but they are not limited thereto:

HT1

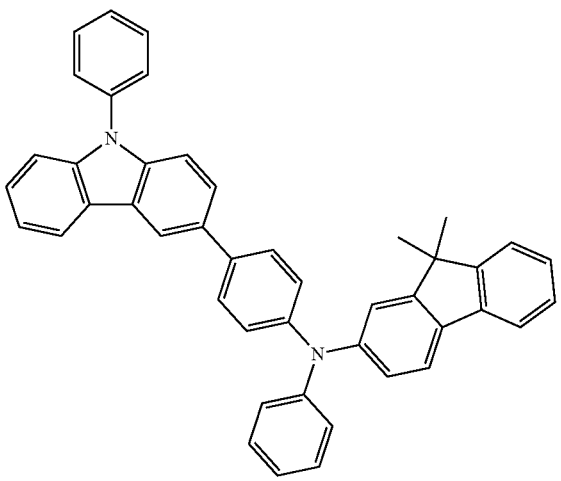

HT2
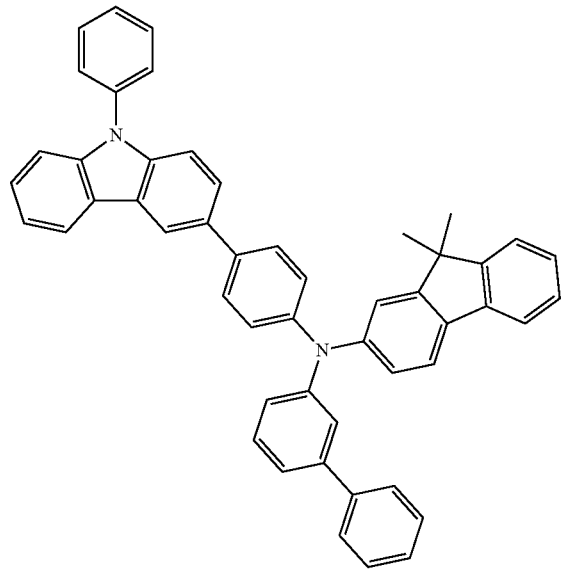
HT4
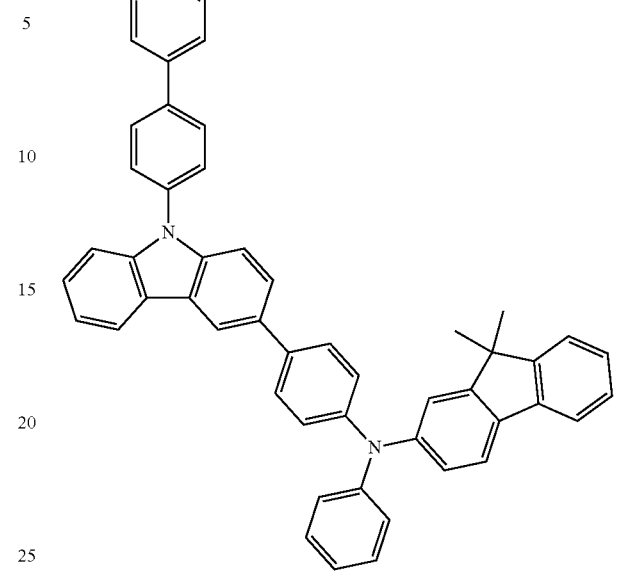
HT3
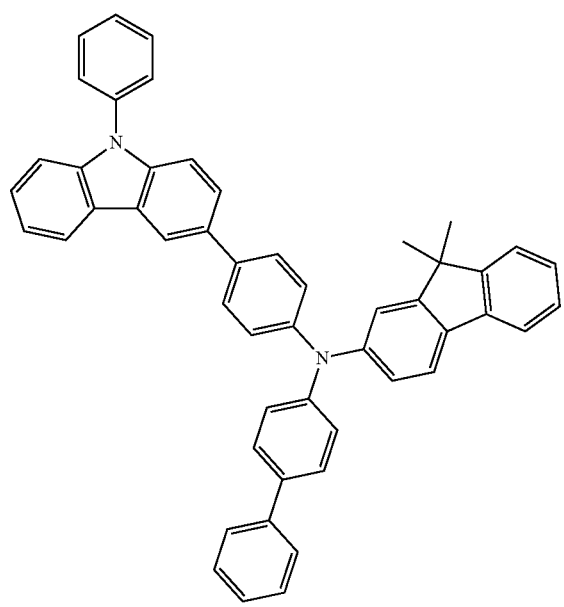
HT5
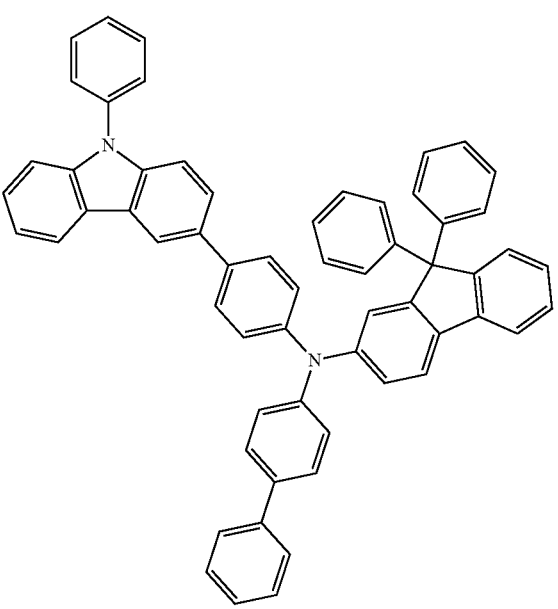

HT6
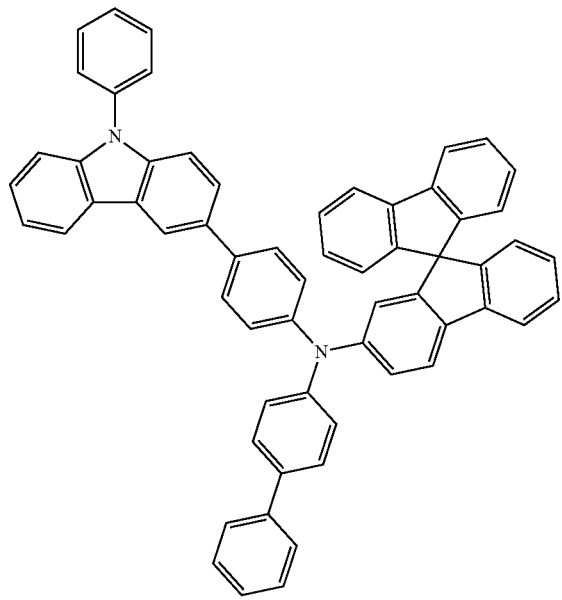
HT7
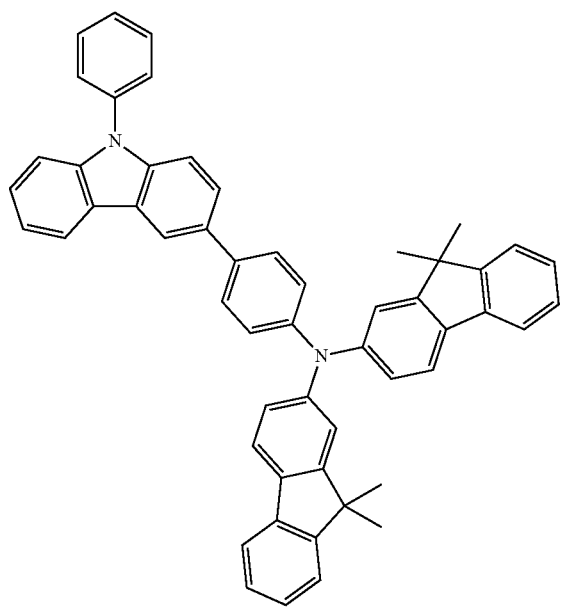
HT8
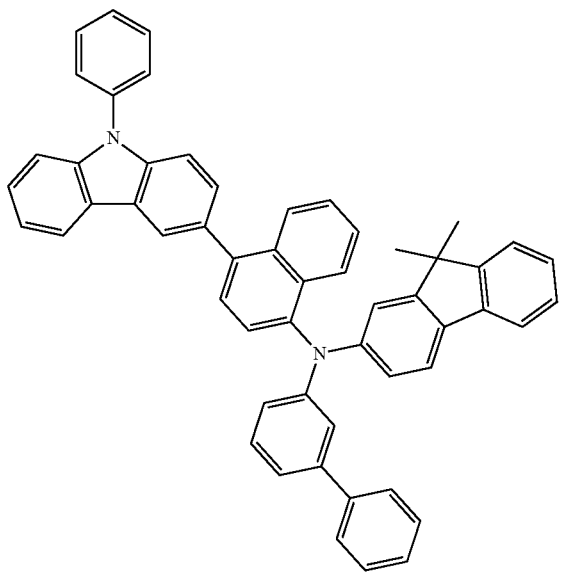
HT9
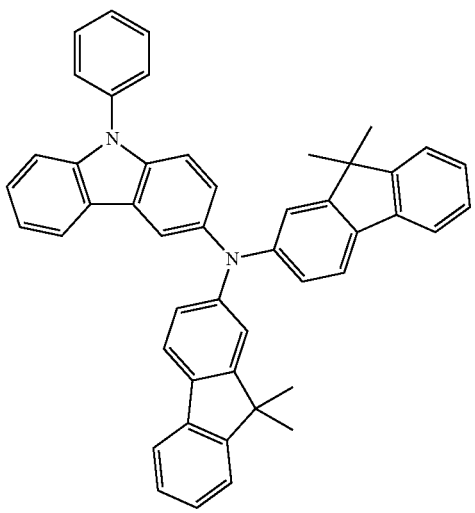

-continued
HT10
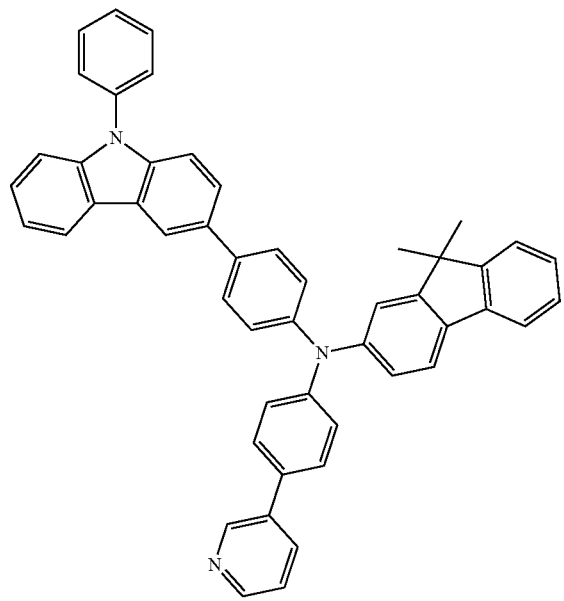
HT11
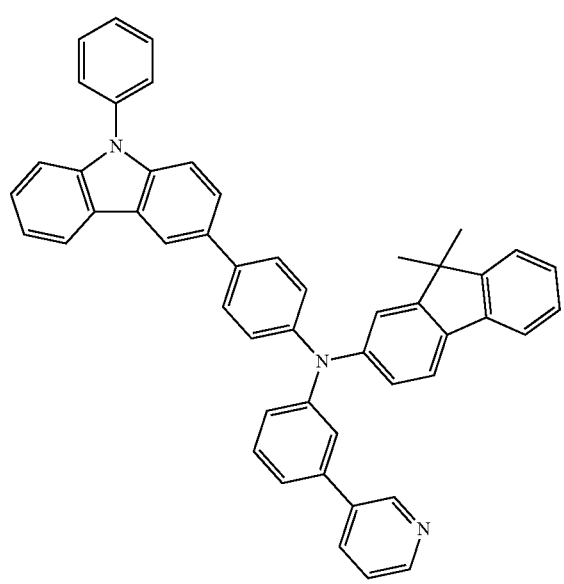
HT12
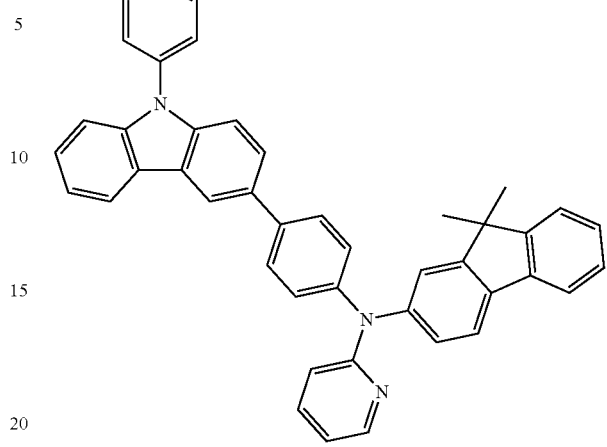
HT13
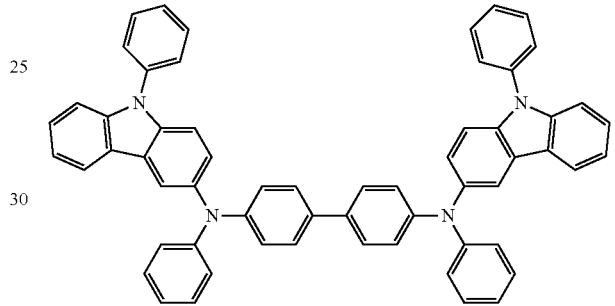
HT14
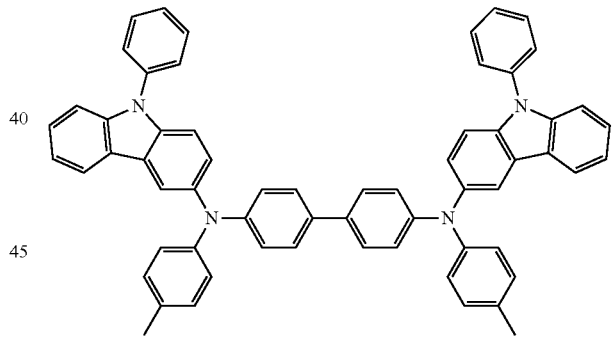
HT15
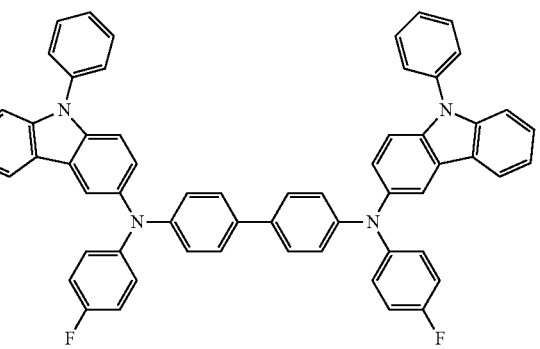

HT16
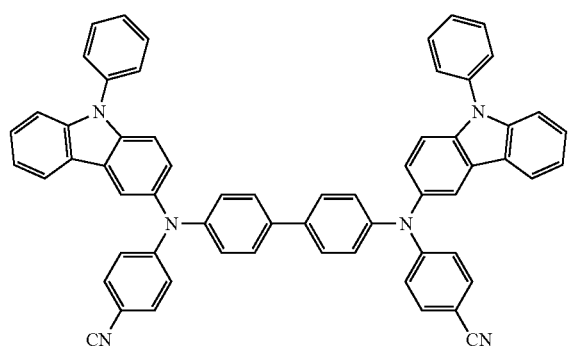

HT17
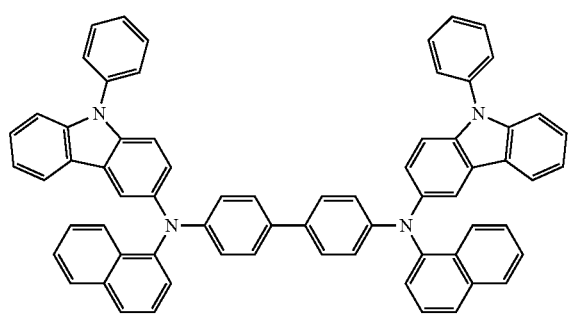

HT18
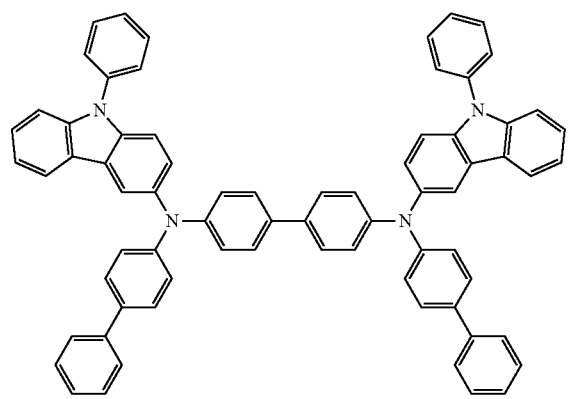

HT19
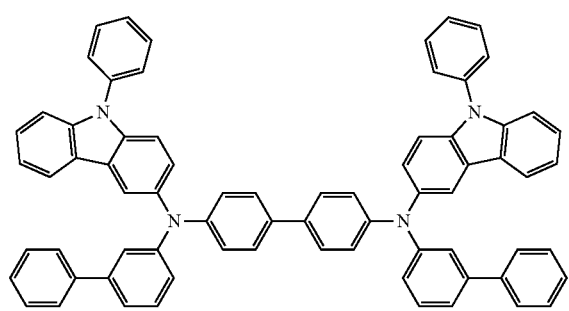

HT20
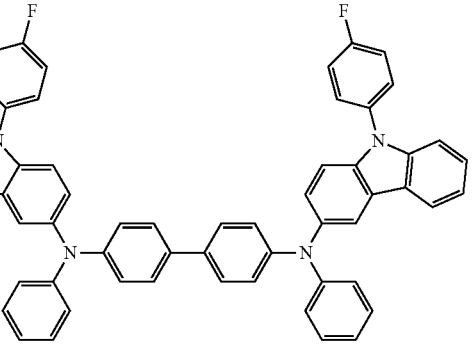

A thickness of the hole transport region may be about 100 Angstroms (Å) to about 10,000 Å, for example, about 100 Å to about 1,000 Å. When the hole transport region includes the HIL and the HTL, a thickness of the HIL may be about 50 Å to about 10,000 Å, for example, about 100 Å to about 1,000 Å, a thickness of the HTL may be about 50 Å to about 2,000 Å, for example, about 100 Å to about 1,500 Å. When the thicknesses of the hole transport region, the HIL, and the HTL are within the ranges described above, satisfactory hole transporting properties may be obtained without a substantial increase in a driving voltage.

The hole transport region may further include, in addition to the above-mentioned materials, a charge-generating material for the improvement of conductive properties. The charge-generating material may be homogeneously or non-homogeneously dispersed throughout the hole transport region.

The charge-generating material may be, for example, a p-dopant. The p-dopant may be one selected from a quinone derivative, a metal oxide, and a cyano group-containing compound, but it is not limited thereto. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and the Compound HT-D1 illustrated below, but it is not limited thereto.

Compound HT-D1
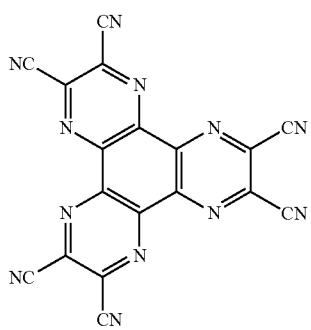

F4-TCNQ
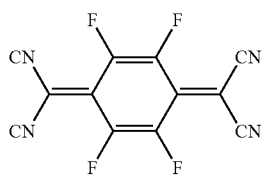

The hole transport region may further include a buffer layer.

The buffer layer may compensate for an optical resonance distance according to a wavelength of light emitted from the EML to improve the efficiency of an organic light-emitting device.

An EML may be formed on the hole transport region by using various methods, such as vacuum deposition, spin coating, casting, or an LB method. When the EML is formed by vacuum deposition or spin coating, deposition and coating conditions for the EML may be similar to the conditions for forming the HIL, though the conditions may vary depending on the compound used.

The EML may include a host and a dopant, and the dopant may include the organometallic compound represented by Formula 1 above.

The host may include at least one selected from TPBi, TBADN, AND (also known as "DNA"), CBP, CDBP, and TCP:

TPBi

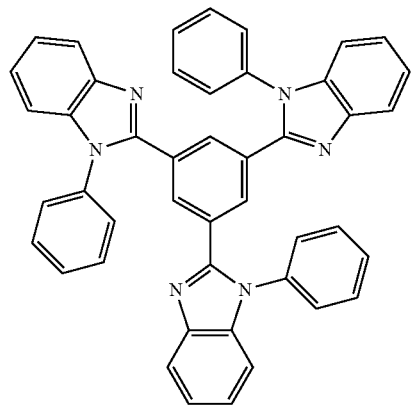

TBADN

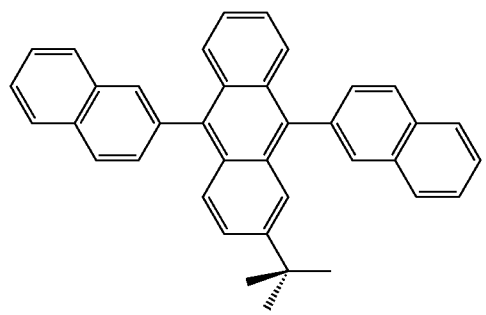

ADN

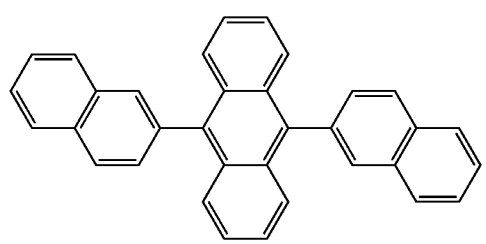

CBP

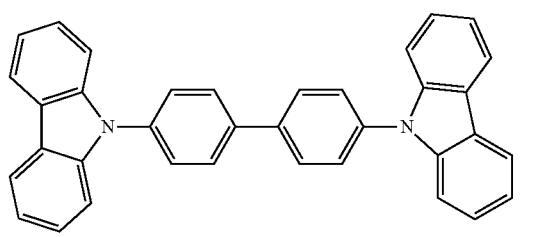

CDBP

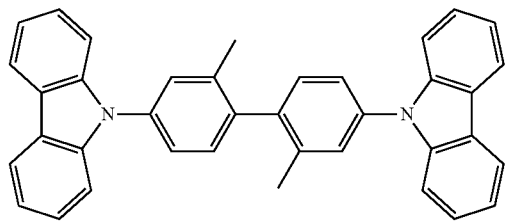

TCP

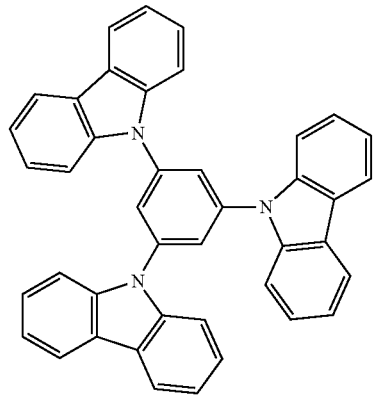

When the EML includes the host and the dopant, the amount of the dopant may be selected from a range of about 0.01 parts by weight to about 15 parts by weight based on 100 parts by weight of the host, but the amount is not limited thereto.

A thickness of the EML may be about 100 Å to about 1,000 Å, for example, about 200 Å to about 600 Å. When the thickness of the EML is within this range, excellent light-emission characteristics may be obtained without a substantial increase in driving voltage.

Then, an electron transport region may be disposed on the EML.

The electron transport region may include at least one selected from an HBL, an ETL, and an EIL, but is not limited thereto.

For example, the electron transport region may have a structure of HBL/ETL/EIL or ETL/EIL, but it is not limited thereto. The ETL may have a single layer structure or a multi-layer structure including two or more different materials.

Conditions for forming the HBL, ETL, and EIL of the electron transport region are as the conditions described for forming the HIL.

When the electron transport region includes an HBL, the HBL may, for example, include at least one selected from BCP and Bphen, but it is not limited thereto.

BCP

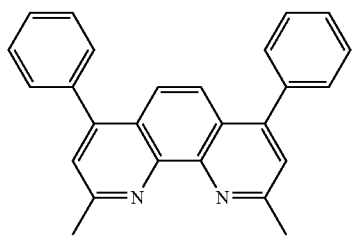

Bphen

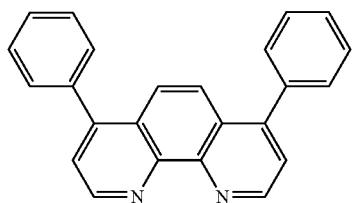

A thickness of the HBL may be in a range of about 20 Å to about 1,000 Å, for example, about 30 Å to about 300 Å. When the thickness of the HBL is within the range described above, the HBL may have excellent hole blocking characteristics without a substantial increase in driving voltage.

The ETL may include at least one selected from BCP and Bphen, and may further include at least one selected from $Alq_3$, Balq, TAZ, and NTAZ.

$Alq_3$

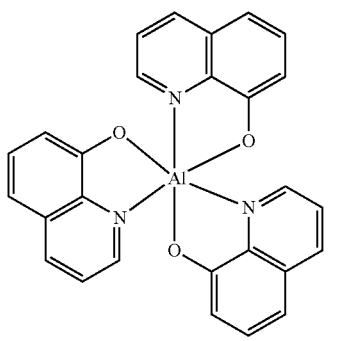

BAlq

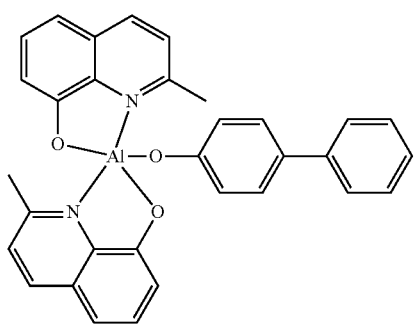

TAZ

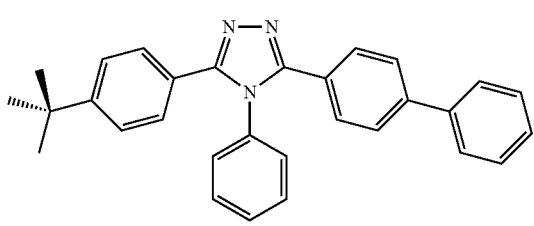

NTAZ

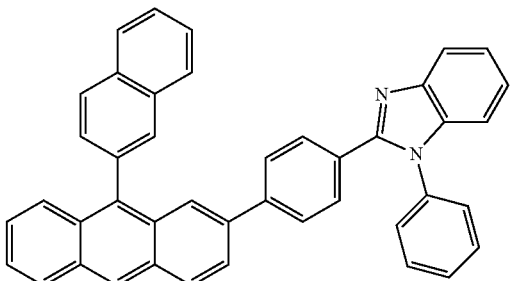

Alternatively, the ETL may include at least one selected from Compounds ET1 and ET2, but it is not limited thereto.

ET1

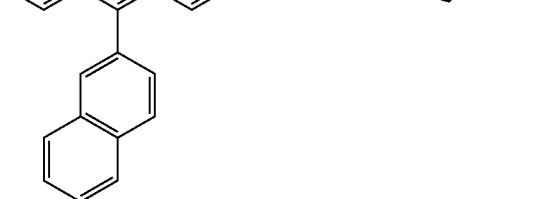

ET2

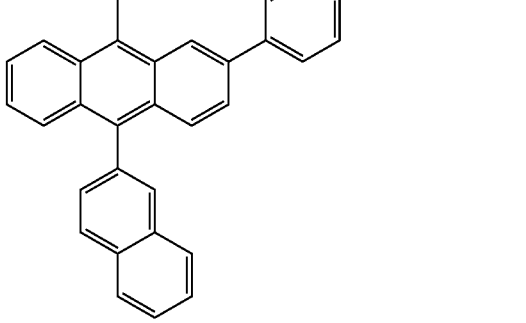

A thickness of the ETL may be in a range of about 100 Å to about 1,000 Å, for example, about 150 Å to about 500 Å. When the thickness of the ETL is within the range described above, the ETL may have satisfactory electron transportation characteristics without a substantial increase in driving voltage.

Also, the ETL may further include, in addition to the materials described above, a metal-containing material.

The metal-containing material may include a Li complex. The Li complex may include, for example, the Compound ET-D1 (lithium quinolate, LiQ) or ET-D2.

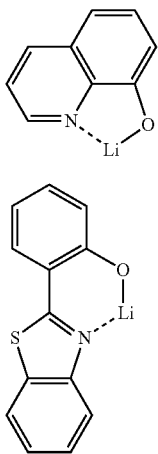

ET-D1

ET-D2

The electron transport region may include an EIL that facilitates electron injection from the second electrode 19.

A thickness of the EIL may be in a range of about 1 Å to about 100 Å, for example, about 3 Å to about 90 Å. When the thickness of the EIL is within the range described above, the EIL may have satisfactory electron transportation characteristics without a substantial increase in driving voltage.

The second electrode 19 is disposed on the organic layer 15 having the structure described above. The second electrode 19 may be a cathode. A material for the second electrode 19 may be a material having a low work function, and such a material may be a metal, an alloy, an electrically conductive compound, or a mixture thereof. Detailed examples of the material for forming the second electrode 19 are Li, Mg, Al, Al—Li, Ca, Mg—In, and Mg—Ag. Alternatively, ITO or IZO may be used to form a transmissive second electrode 19 to manufacture a top emission light-emitting device.

Hereinbefore, the organic light-emitting device has been described with reference to the FIGURE, but the organic light-emitting device is not limited thereto.

A $C_1$-$C_{60}$ alkyl group used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene used herein refers to a divalent group having the same structure as the $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group). Detailed examples thereof are a methoxy group, an ethoxy group, and an isopropoxy group.

A $C_2$-$C_{60}$ alkenyl group used herein refers to a hydrocarbon group formed by substituting at least one carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group used herein refers to a divalent group having the same structure as the $C_2$-$C_{60}$ alkenyl group.

A $C_2$-$C_{60}$ alkynyl group used herein refers to a hydrocarbon group formed by substituting at least one carbon triple bond in the middle or at the terminal of the $C_2$-$C_{60}$ alkyl group. Detailed examples thereof are an ethynyl group and a propynyl group. A $C_2$-$C_{60}$ alkynylene group used herein refers to a divalent group having the same structure as the $C_2$-$C_{60}$ alkynyl group.

A $C_3$-$C_{10}$ cycloalkyl group used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_3$-$C_{10}$ heterocycloalkyl group used herein refers to a monovalent monocyclic group having at least one heteroatom selected from N, O, P, and S as a ring-forming atom and 3 to 10 carbon atoms. Detailed examples thereof are tetrahydrofuranyl and tetrahydrothiophenyl. A $C_3$-$C_{10}$ heterocycloalkylene group used herein refers to a divalent group having the same structure as the $C_3$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof, and which is not aromatic. Detailed examples thereof are a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_2$-$C_{10}$ heterocycloalkenyl group used herein refers to a monovalent monocyclic group that has at least one heteroatom selected from N, O, P, and S as a ring-forming atom, 2 to 10 carbon atoms, and at least one double bond in its ring. Detailed examples of the $C_2$-$C_{10}$ heterocycloalkenyl group are a 2,3-dihydrofuranyl group and a 2,3-dihydrothiophenyl group. A $C_2$-$C_{10}$ heterocycloalkenylene group used herein refers to a divalent group having the same structure as the $C_2$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_2$-$C_{60}$ heteroaryl group used herein refers to a monovalent group having a carbocyclic aromatic system that has at least one heteroatom selected from N, O, P, and S as a ring-forming atom, and 2 to 60 carbon atoms. A $C_2$-$C_{60}$ heteroarylene group used herein refers to a divalent group having a carbocyclic aromatic system that has at least one heteroatom selected from N, O, P, and S as a ring-forming atom, and 2 to 60 carbon atoms. Detailed examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. If the $C_2$-$C_{60}$ heteroaryl group and the $C_2$-$C_{60}$ heteroarylene group each include two or more rings, the rings may be fused to each other.

A $C_6$-$C_{60}$ aryloxy group used herein indicates —$OA_{102}$ (wherein $A_{102}$ is the $C_6$-$C_{60}$ aryl) and a $C_6$-$C_{60}$ arylthio group used herein indicates —$SA_{103}$ (wherein $A_{103}$ is the $C_6$-$C_{60}$ aryl group).

A monovalent non-aromatic condensed polycyclic group (for example, having 8 to 60 carbon atoms) used herein refers to a monovalent group that has two or more rings condensed to each other, only carbon atoms as ring-forming atoms, and which is non-aromatic in the entire molecular structure. A detailed example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group (for example, having 2 to 60 carbon atoms) used herein refers to a monovalent group that has two or more rings condensed to each other, has a heteroatom selected from N, O P, and S, other than carbon atoms, as a ring forming atom, and which is non-aromatic in the entire molecular structure. Detailed examples of the monovalent non-aromatic condensed heteropolycyclic group are a carbazolyl group. A divalent non-aromatic condensed heteropolycyclic group used herein refers to a divalent group having the same structure as the monovalent non-aromatic condensed heteropolycyclic group.

As used herein, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$) and —B($Q_{36}$)($Q_{37}$);
wherein $Q_1$ to $Q_7$, $Q_{11}$ to $Q_{17}$, $Q_{21}$ to $Q_{27}$, and $Q_{31}$ to $Q_{37}$ may be each independently hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

According to an embodiment, as used herein, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a cyclopentyl group, a cyclohexyl group, a cycloheptyl group, a cyclopentenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, $N(Q_{11})(Q_{12})$, $-Si(Q_{13})(Q_{14})(Q_{15})$, and $-B(Q_{16})(Q_{17})$;

a cyclopentyl group, a cyclohexyl group, a cycloheptyl group, a cyclopentenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclopentenyl group, a cycloheplenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluoronyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl, a $C_2$-$C_{60}$ alkenyl, a $C_2$-$C_{60}$ alkynyl, a $C_1$-$C_{60}$ alkoxy, phenyl, naphthyl, $-N(Q_{21})(Q_{22})$, $-Si(Q_{23})(Q_{24})(Q_{25})$, and $-B(Q_{26})(Q_{27})$; and $-N(Q_{31})(Q_{32})$, $-Si(Q_{33})(Q_{34})(Q_{35})$, and $-B(Q_{36})(Q_{37})$; wherein, $Q_{11}$ to $Q_{17}$, $Q_{21}$ to $Q_{27}$, and $Q_{31}$ to $Q_{37}$ may be each independently hydrogen, a $C_1$-$C_{60}$ alkyl, a $C_2$-$C_{60}$ alkenyl, a $C_2$-$C_{60}$ alkynyl, a $C_1$-$C_{60}$ alkoxy, a cyclopentyl group, a cyclohexyl group, a cycloheptyl group, a cyclopentenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl, an imidazopyridinyl group, and an imidazopyrimidinyl group.

Hereinafter, an organic light-emitting device according to an embodiment will be described in detail with reference to Synthesis Examples and Examples. The wording "B was used instead of A" used in describing Synthesis Examples means that the molar amount of B used was identical to the molar amount of A.

EXAMPLES

Synthesis Example 1

Synthesis of Compound 1

Synthesis of Ligand 1(1)

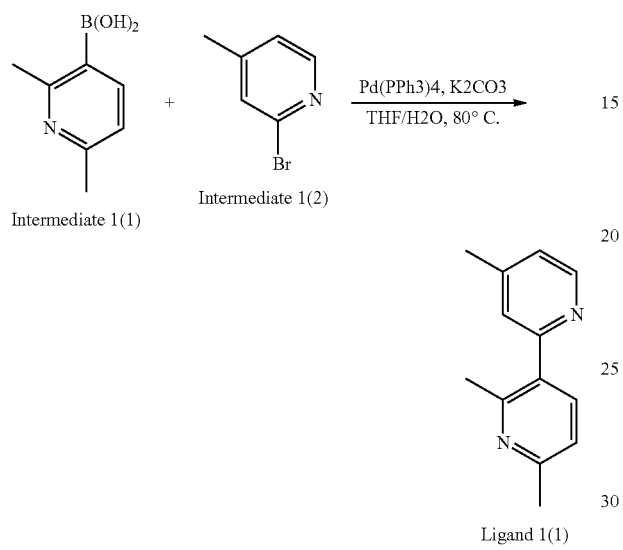

22.5 grams (g) of Intermediate 1(1) (0.15 moles (mol)) and 25.8 g of Intermediate 1(2) (0.15 mol) were mixed with 200 milliliters (mL) of THF in a 1 liter (L) round bottom flask loaded with an agitator under a nitrogen atmosphere. 150 mL of 2 molar (M) potassium carbonate aqueous solution, followed by 6 g of tetrakis(triphenylphosphine) palladium(0) (36.68 mmol) was added, and the resulting mixture was heated under reflux for 12 hours under a nitrogen atmosphere. After completion of the reaction, the organic layer was separated from the mixture. The solvent was removed therefrom, and column chromatography was used to obtain 20.8 g of Ligand 1(1) (yield of 70%).

Synthesis of Intermediate 1(4)

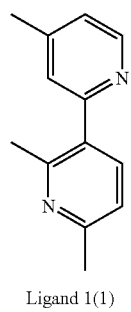

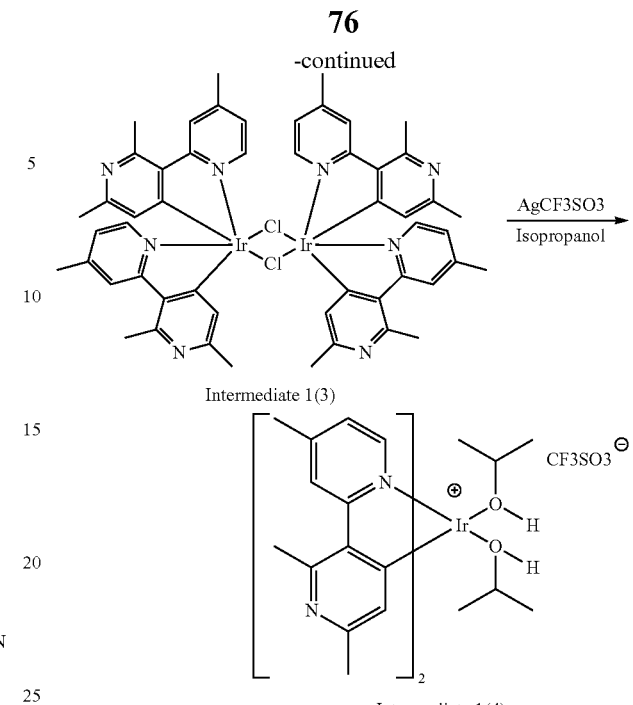

19.9 g (0.1 mol) of Ligand 1(1), 13.16 g of iridium chloride (0.044 mol), 180 mL of THF, and 55 mL of distilled water were mixed together and heated under reflux for 20 hours to obtain Intermediate 1(3). 11.31 g of AgCF$_3$SO$_3$ (0.044 mol) and 200 mL of isopropanol were added to Intermediate 1(3), and the product obtained therefrom was heated under reflux to for 12 hours to obtain 32 g of Intermediate 1(4) (yield of 86%).

Synthesis of Compound 1

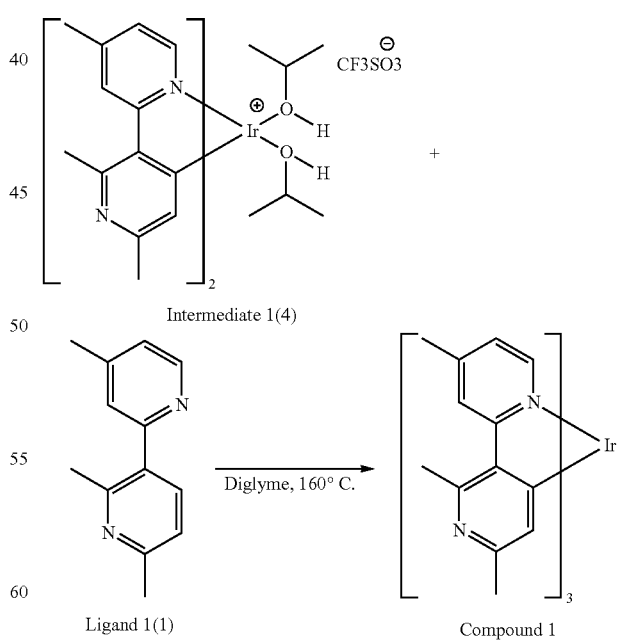

32 g of Intermediate 1(4) (0.037 mol), 7.33 g of Ligand 1(1) (0.037 mol), and 250 mL of diglyme were heat refluxed in a 1 L round bottom flask to obtain 23.5 g of Compound 1 (yield of 81%).

¹H NMR (300 MHz, CDCl₃, rt): δ 8.66 (d, J=8.50 Hz, 4 H), 8.02 (d, J=7.35 Hz, 2 H), 7.41-7.55 (m, 4 H), 7.12 (d, J=7.30, 2 H), 3.15 (s, 9 H), 2.53 (s, 9 H), 2.35 (s, 9 H).

Synthesis Example 2

Synthesis of Compound 2 except that Intermediate 2(1) and Intermediate 2(2) were used instead of Intermediate 1(1) and Intermediate 1(2), respectively.

Synthesis of Intermediate 2(4)

Ligand 2(4) was synthesized in the same manner as in the synthesis method of Intermediate 1(4) in Synthesis Example 1, except that Ligand 2(1) was used instead of Ligand 1(1).

Synthesis of Compound 2

10 g of Compound 2 (synthesis yield of 35%) was synthesized in the same manner as in the synthesis method of Compound 1 in Synthesis Example 1, except that Intermediate 2(4) and Ligand 2(1) were used instead of Intermediate 1(4) and Ligand 1(1), respectively.

¹H NMR (300 MHz, CDCl₃, rt): δ 8.32 (d, J=8.05 Hz, 2 H), 8.0 (d, J=7.50 Hz, 2 H), 7.82-7.90 (m, 3 H), 7.56 (d, J=7.05 Hz, 2 H), 7.01-7.26 (m, 4 H), 5.80 (d, J=7.35 Hz, 2 H), 2.60 (s, 27 H), 2.58 (d, 27 H).

Synthesis Example 3

Synthesis of Compound 3

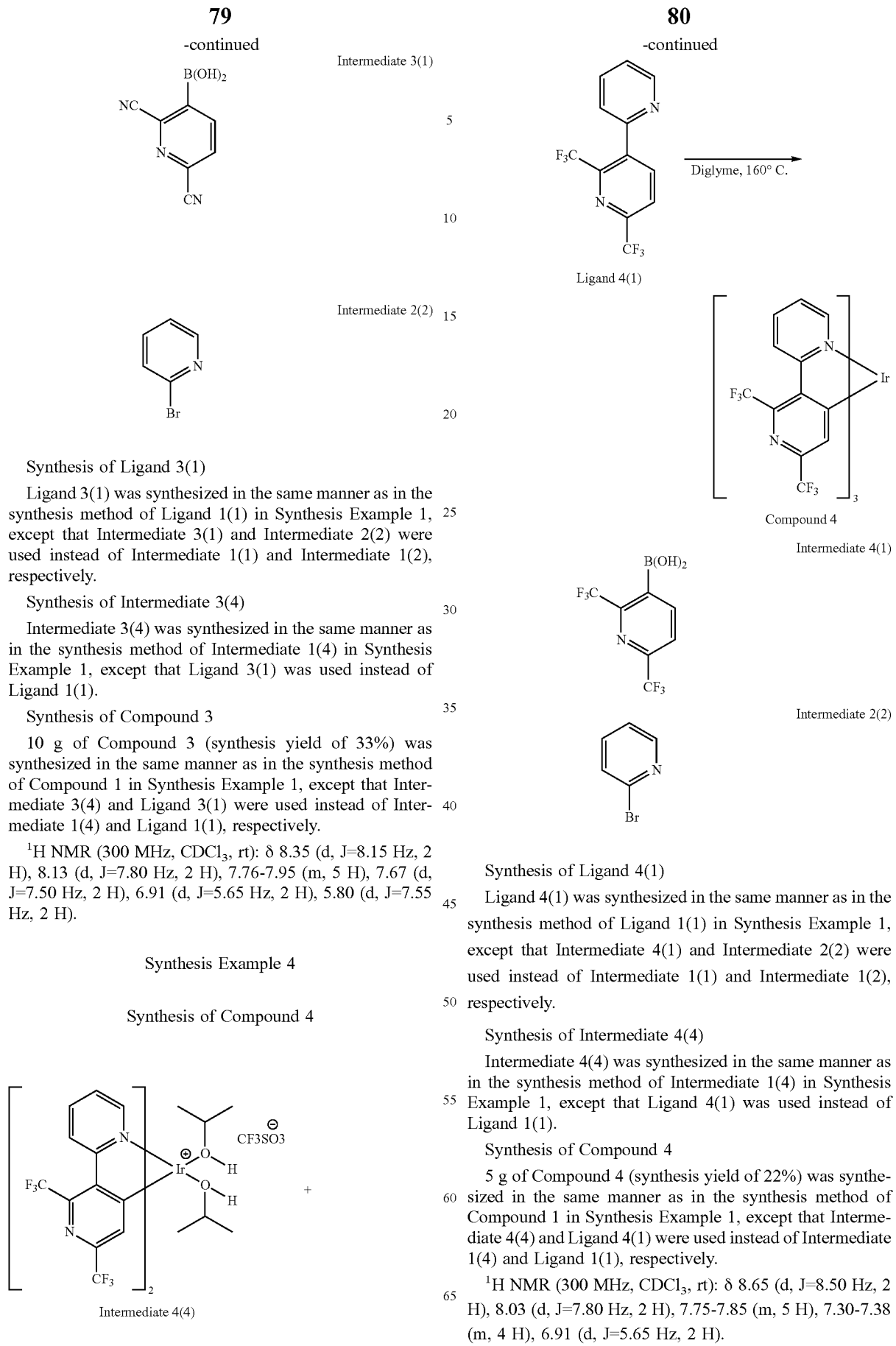

Synthesis of Ligand 3(1)

Ligand 3(1) was synthesized in the same manner as in the synthesis method of Ligand 1(1) in Synthesis Example 1, except that Intermediate 3(1) and Intermediate 2(2) were used instead of Intermediate 1(1) and Intermediate 1(2), respectively.

Synthesis of Intermediate 3(4)

Intermediate 3(4) was synthesized in the same manner as in the synthesis method of Intermediate 1(4) in Synthesis Example 1, except that Ligand 3(1) was used instead of Ligand 1(1).

Synthesis of Compound 3

10 g of Compound 3 (synthesis yield of 33%) was synthesized in the same manner as in the synthesis method of Compound 1 in Synthesis Example 1, except that Intermediate 3(4) and Ligand 3(1) were used instead of Intermediate 1(4) and Ligand 1(1), respectively.

$^1$H NMR (300 MHz, CDCl$_3$, rt): δ 8.35 (d, J=8.15 Hz, 2 H), 8.13 (d, J=7.80 Hz, 2 H), 7.76-7.95 (m, 5 H), 7.67 (d, J=7.50 Hz, 2 H), 6.91 (d, J=5.65 Hz, 2 H), 5.80 (d, J=7.55 Hz, 2 H).

Synthesis Example 4

Synthesis of Compound 4

Synthesis of Ligand 4(1)

Ligand 4(1) was synthesized in the same manner as in the synthesis method of Ligand 1(1) in Synthesis Example 1, except that Intermediate 4(1) and Intermediate 2(2) were used instead of Intermediate 1(1) and Intermediate 1(2), respectively.

Synthesis of Intermediate 4(4)

Intermediate 4(4) was synthesized in the same manner as in the synthesis method of Intermediate 1(4) in Synthesis Example 1, except that Ligand 4(1) was used instead of Ligand 1(1).

Synthesis of Compound 4

5 g of Compound 4 (synthesis yield of 22%) was synthesized in the same manner as in the synthesis method of Compound 1 in Synthesis Example 1, except that Intermediate 4(4) and Ligand 4(1) were used instead of Intermediate 1(4) and Ligand 1(1), respectively.

$^1$H NMR (300 MHz, CDCl$_3$, rt): δ 8.65 (d, J=8.50 Hz, 2 H), 8.03 (d, J=7.80 Hz, 2 H), 7.75-7.85 (m, 5 H), 7.30-7.38 (m, 4 H), 6.91 (d, J=5.65 Hz, 2 H).

Synthesis Example 5

Synthesis of Compound 5

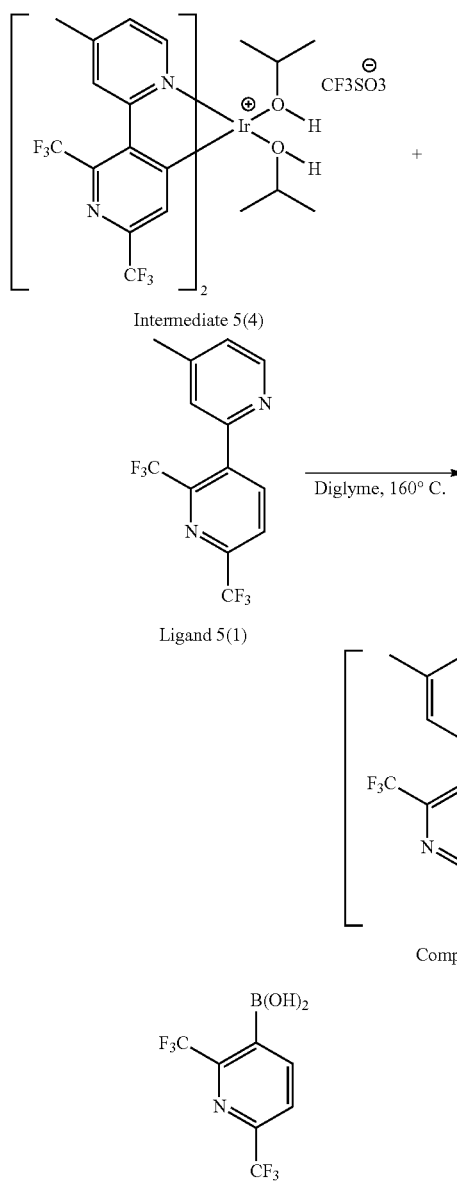

Synthesis of Ligand 5(1)

Ligand 5(1) was synthesized in the same manner as in the synthesis method of Ligand 1(1) in Synthesis Example 1, except that Intermediate 5(1) was used instead of Intermediate 1(1).

Synthesis of Intermediate 5(4)

Ligand 5(4) was synthesized in the same manner as in the synthesis method of Intermediate 1(4) in Synthesis Example 1, except that Ligand 5(1) was used instead of Ligand 1(1).

Synthesis of Compound 5

5 g of Compound 5 (synthesis yield of 19%) was synthesized in the same manner as in the synthesis method of Compound 1 in Synthesis Example 1, except that Intermediate 5(4) and Ligand 5(1) were used instead of Intermediate 1(4) and Ligand 1(1), respectively.

$^1$H NMR (300 MHz, CDCl$_3$, rt): δ 8.60 (d, J=8.50 Hz, 2 H), 8.14 (d, J=7.50 Hz, 2 H), 7.70-7.83 (m, 4 H), 7.35-7.45 (m, 2 H), 6.68 (d, J=7.60 Hz, 2 H), 3.15 (s, 9H).

Synthesis Example 6

Synthesis of Compound 6

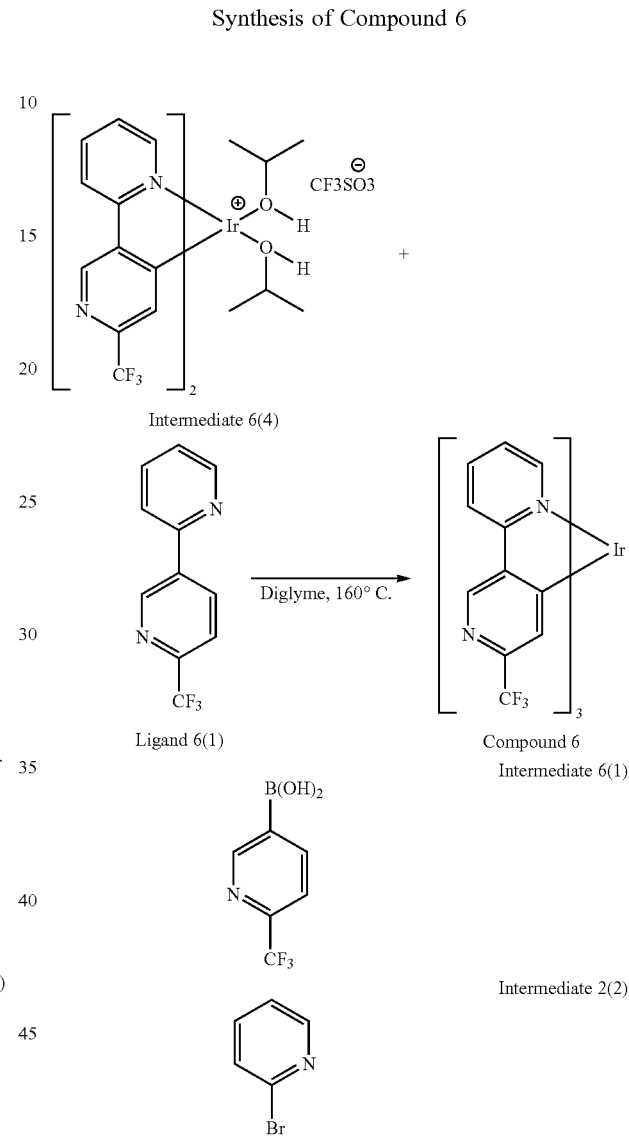

Synthesis of Ligand 6(1)

Ligand 6(1) was synthesized in the same manner as in the synthesis method of Ligand 1(1) in Synthesis Example 1, except that Intermediate 6(1) and Intermediate 2(2) were used instead of Intermediate 1(1) and Intermediate 1(2), respectively.

Synthesis of Intermediate 6(4)

Intermediate 6(4) was synthesized in the same manner as in the synthesis method of Intermediate 1(4) in Synthesis Example 1, except that Ligand 6(1) was used instead of Ligand 1(1).

Synthesis of Compound 6

3 g of Compound 6 (synthesis yield of 18%) was synthesized in the same manner as in the synthesis method of Compound 1 in Synthesis Example 1, except that Intermediate 6(4) and Ligand 6(1) were used instead of Intermediate 1(4) and Ligand 1(1), respectively.

$^1$H NMR (300 MHz, CDCl$_3$, rt): δ 9.15 (d, J=8.59 Hz, 2 H), 8.63 (d, J=8.50 Hz, 2 H), 8.13 (d, J=7.75 Hz, 2 H), 7.74-7.87 (m, 4 H), 7.33-7.42 (m, 6 H), 6.94 (d, J=5.65 Hz, 2 H).

Synthesis Example 7

Synthesis of Compound 7

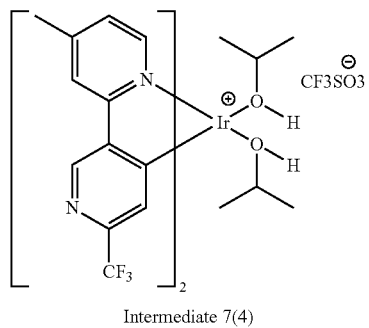

Intermediate 7(4)

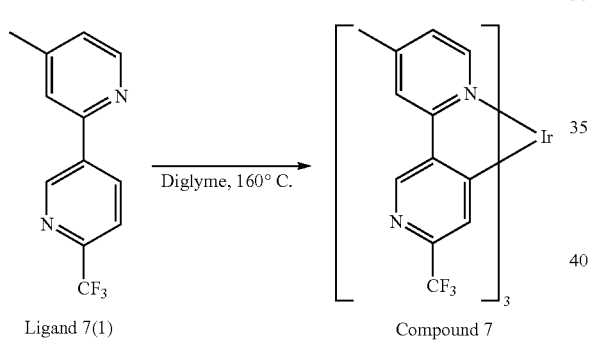

Ligand 7(1)    Compound 7

Synthesis of Ligand 7(1)

Ligand 7(1) was synthesized in the same manner as in the synthesis method of Ligand 1(1) in Synthesis Example 1, except that Intermediate 6(1) was used instead of Intermediate 1(1).

Synthesis of Intermediate 7(4)

Intermediate 7(4) was synthesized in the same manner as in the synthesis method of Intermediate 1(4) in Synthesis Example 1, except that Ligand 7(1) was used instead of Ligand 1(1).

Synthesis of Compound 7

3 g of Compound 7 (synthesis yield of 8%) was synthesized in the same manner as in the synthesis method of Compound 1 in Synthesis Example 1, except that Intermediate 7(4) and Ligand 7(1) were used instead of Intermediate 1(4) and Ligand 1(1), respectively.

$^1$H NMR (300 MHz, CDCl$_3$, rt): δ 9.09 (d, J=8.55 Hz, 2 H), 8.66 (d, J=8.45 Hz, 2 H), 8.02 (d, J=7.66 Hz, 2 H), 7.72-7.68 (m, 3 H), 7.30-7.39 (m, 4 H), 7.02 (d, J=5.65 Hz, 2 H), 2.36 (s, 9 H).

Synthesis Example 8

Synthesis of Compound 8

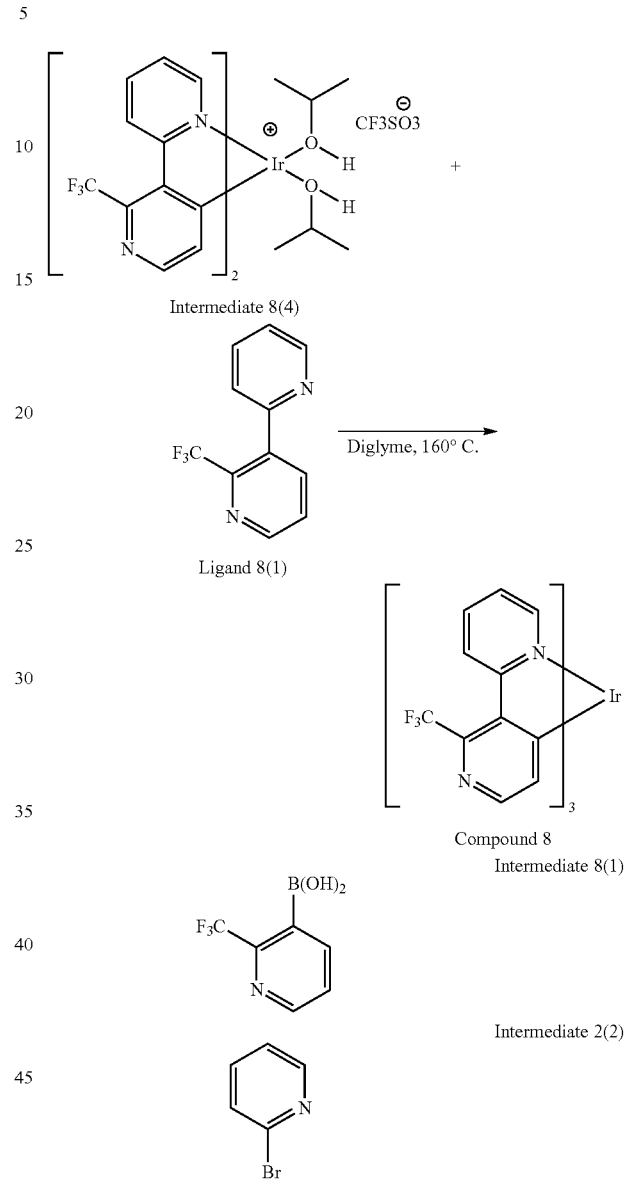

Synthesis of Ligand 8(1)

Ligand 8(1) was synthesized in the same manner as in the synthesis method of Ligand 1(1) in Synthesis Example 1, except that Intermediate 8(1) and Intermediate 2(2) were used instead of Intermediate 1(1) and Intermediate 1(2), respectively.

Synthesis of Intermediate 8(4)

Intermediate 8(4) was synthesized in the same manner as in the synthesis method of Intermediate 1(4) in Synthesis Example 1, except that Ligand 8(1) was used instead of Ligand 1(1).

Synthesis of Compound 8

3 g of Compound 8 (synthesis yield of 25%) was synthesized in the same manner as in the synthesis method of Compound 1 in Synthesis Example 1, except that Intermediate 8(4) and Ligand 8(1) were used instead of Intermediate 1(4) and Ligand 1(1), respectively.

$^1$H NMR (300 MHz, CDCl$_3$, rt): δ 8.65 (d, J=8.59 Hz, 2 H), 8.43 (d, J=8.50 Hz, 2 H), 8.03 (d, J=7.36 Hz, 2 H), 7.58-7.85 (m, 6 H), 7.30-7.39 (m, 6 H).

Synthesis Example 9

Synthesis of Compound 9

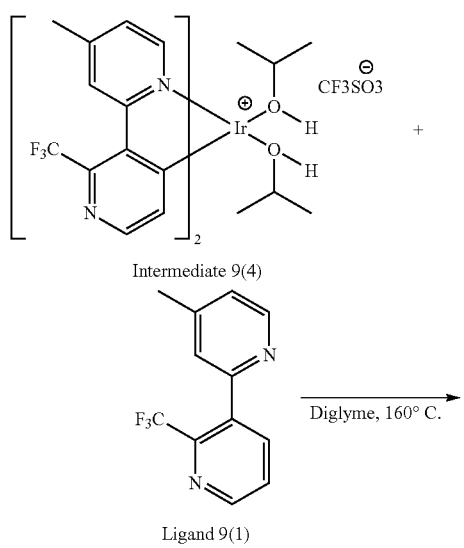

Synthesis Example 10

Synthesis of Compound 12

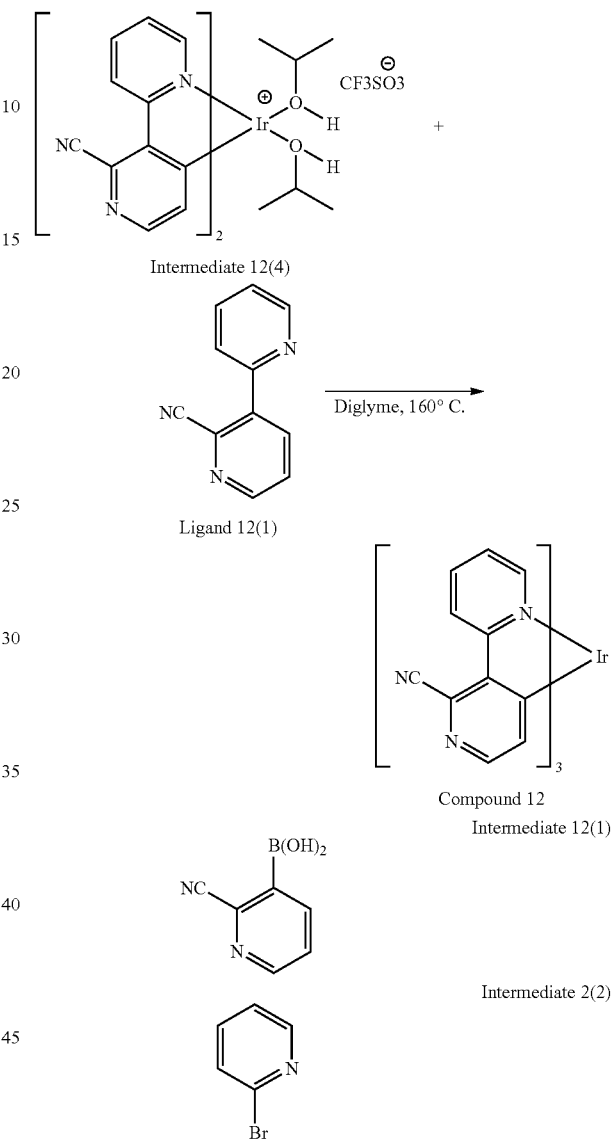

Synthesis of Ligand 9(1)

Ligand 9(1) was synthesized in the same manner as in the synthesis method of Ligand 1(1) in Synthesis Example 1, except that Intermediate 9(1) was used instead of Intermediate 1(1).

Synthesis of Intermediate 9(4)

Intermediate 9(4) was synthesized in the same manner as in the synthesis method of Intermediate 1(4) in Synthesis Example 1, except that Ligand 9(1) was used instead of Ligand 1(1).

Synthesis of Compound 9

3 g of Compound 9 was synthesized in the same manner as in the synthesis method of Compound 1 in Synthesis Example 1, except that Intermediate 9(4) and Ligand 9(1) were used instead of Intermediate 1(4) and Ligand 1(1), respectively.

$^1$H NMR (300 MHz, CDCl$_3$, rt): δ 8.66 (d, J=8.60 Hz, 2 H), 8.44 (d, J=8.45 Hz, 2 H), 8.05 (d, J=7.38 Hz, 2 H), 7.68-7.76 (m, 4 H), 7.28-7.38 (m, 5 H), 2.35 (s, 9 H).

Synthesis of Ligand 12(1)

Ligand 12(1) was synthesized in the same manner as in the synthesis method of Ligand 1(1) in Synthesis Example 1, except that Intermediate 12(1) and Intermediate 2(2) were used instead of Intermediate 1(1) and Intermediate 1(2), respectively.

Synthesis of Intermediate 12(4)

Intermediate 12(4) was synthesized in the same manner as in the synthesis method of Intermediate 1(4) in Synthesis Example 1, except that Ligand 12(1) was used instead of Ligand 1(1).

Synthesis of Compound 12

3 g of Compound 12 (Synthesis yield of 10%) was synthesized in the same manner as in the synthesis method of Compound 1 in Synthesis Example 1, except that Intermediate 12(4) and Ligand 12(1) were used instead of Intermediate 1(4) and Ligand 1(1), respectively.

$^1$H NMR (300 MHz, CDCl$_3$, rt): δ 8.82 (d, J=8.59 Hz, 2 H), 8.64 (d, J=8.50 Hz, 2 H), 8.02 (d, J=7.36 Hz, 2 H), 7.48-7.85 (m, 6 H), 7.30-7.40 (m, 6 H).

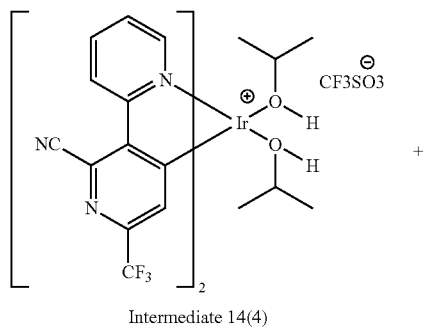

Intermediate 14(4)

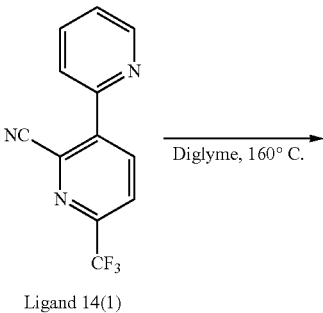

Ligand 14(1)

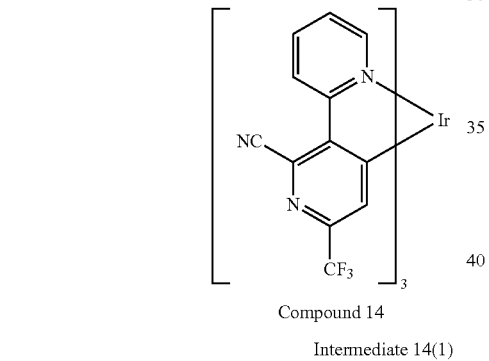

Compound 14
Intermediate 14(1)

Intermediate 2(2)

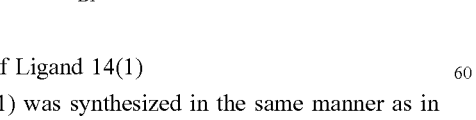

Synthesis of Ligand 14(1)

Ligand 14(1) was synthesized in the same manner as in the synthesis method of Ligand 1(1) in Synthesis Example 1, except that Intermediate 14(1) and Intermediate 2(2) were used instead of Intermediate 1(1) and Intermediate 1(2), respectively.

Synthesis of Intermediate 14(4)

Intermediate 14(4) was synthesized in the same manner as in the synthesis method of Intermediate 1(4) in Synthesis Example 1, except that Ligand 14(1) was used instead of Ligand 1(1).

Synthesis of Compound 14

5 g of Compound 14 (Synthesis yield of 12%) was synthesized in the same manner as in the synthesis method of Compound 1 in Synthesis Example 1, except that Intermediate 14(4) and Ligand 14(1) were used instead of Intermediate 1(4) and Ligand 1(1), respectively.

$^1$H NMR (300 MHz, CDCl$_3$, rt): δ 8.65 (d, J=8.50 Hz, 2 H), 8.03 (d, J=7.80 Hz, 2 H), 7.85-7.94 (m, 5 H), 7.30-7.38 (m, 6 H).

Synthesis Example 12

Synthesis of Compound 15

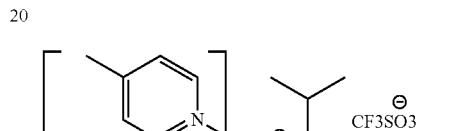

Intermediate 15(4)

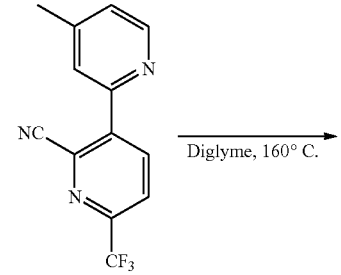

Ligand 15(1)

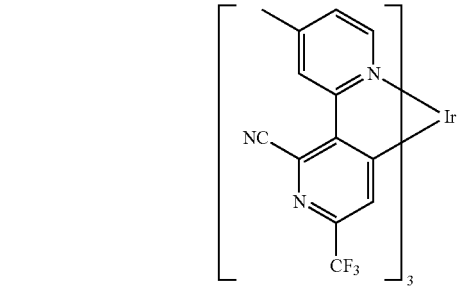

Compound 15
Intermediate 15(1)

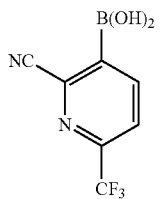

Synthesis of Ligand 15(1)

Ligand 15(1) was synthesized in the same manner as in the synthesis method of Ligand 1(1) in Synthesis Example 1, except that Intermediate 15(1) was used instead of Intermediate 1(1).

Synthesis of Intermediate 15(4)

Intermediate 15(4) was synthesized in the same manner as in the synthesis method of Intermediate 1(4) in Synthesis Example 1, except that Ligand 15(1) was used instead of Ligand 1(1).

Synthesis of Compound 15

3 g of Compound 15 (Synthesis yield of 11%) was synthesized in the same manner as in the synthesis method of Compound 1 in Synthesis Example 1, except that Intermediate 15(4) and Ligand 15(1) were used instead of Intermediate 1(4) and Ligand 1(1), respectively.

$^1$H NMR (300 MHz, CDCl$_3$, rt): δ 8.67 (d, J=8.55 Hz, 2 H), 8.05 (d, J=7.73 Hz, 2 H), 7.85-7.96 (m, 5 H), 7.31-7.39 (m, 6 H), 3.13 (s, 9 H).

Synthesis Example 13

Synthesis of Compound 17

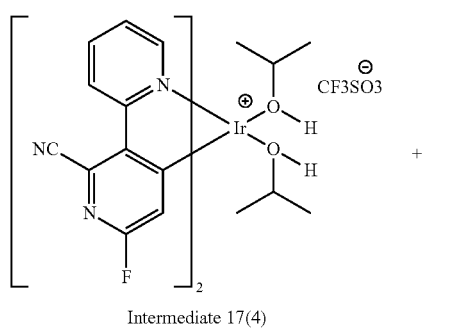
Intermediate 17(4)

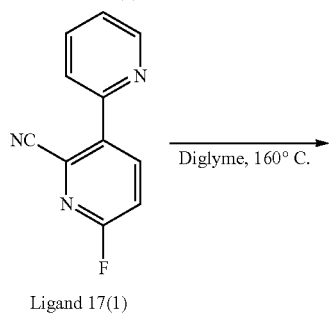
Ligand 17(1)

Diglyme, 160° C.

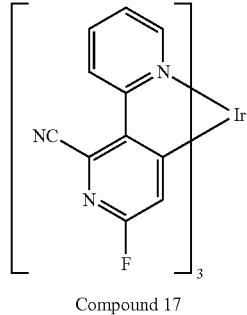
Compound 17

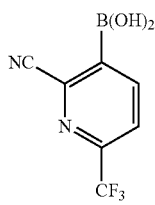
Intermediate 17(1)

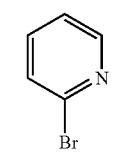
Intermediate 2(2)

Synthesis of Ligand 17(1)

Ligand 17(1) was synthesized in the same manner as in the synthesis method of Ligand 1(1) in Synthesis Example 1, except that Intermediate 17(1) and Intermediate 2(2) were used instead of Intermediate 1(1) and Intermediate 1(2), respectively.

Synthesis of Intermediate 17(4)

Intermediate 17(4) was synthesized in the same manner as in the synthesis method of Intermediate 1(4) in Synthesis Example 1, except that Ligand 17(1) was used instead of Ligand 1(1).

Synthesis of Compound 17

5 g of Compound 17 (Synthesis yield of 15%) was synthesized in the same manner as in the synthesis method of Compound 1 in Synthesis Example 1, except that Intermediate 17(4) and Ligand 17(1) were used instead of Intermediate 1(4) and Ligand 1(1), respectively.

$^1$H NMR (300 MHz, CDCl$_3$, rt): δ 8.68 (d, J=8.50 Hz, 2 H), 8.08 (d, J=7.80 Hz, 2 H), 7.82-7.96 (m, 5 H), 7.30-7.43 (m, 6 H).

Evaluation Example 1

Evaluation of HOMO, LUMO, Triplet (T1) Energy and Maximum Emission Wavelength

Methods described in Table 1 below were used to measure the HOMO energy level, LUMO energy level, triplet energy, and maximum emission wavelength of each compound below.

TABLE 1

| Method of measuring HOMO energy level | Cyclic voltammetry (CV) (electrolyte: 0.1M Bu$_4$NClO$_4$/solvent: CH$_2$Cl$_2$)/ electrode: 3-electrode system (working electrode: GC, reference electrode: Ag/AgCl, auxiliary electrode: Pt)) was used to obtain a voltage (volts, V) - current (amperes, A) graph of each compound and the HOMO energy level of the compound was calculated from the reduction onset in the graph. |
|---|---|
| Method of measuring LUMO energy level | Each compound was diluted in CHCl$_3$ to a concentration of $1 \times 10^{-5}$M and its UV absorption spectrum was measured at room temperature by using a Shimadzu UV-350 spectrometer and the LUMO energy level was calculated from edges of the absorption spectrum by using an optical band gap (Eg). |
| Method of measuring triplet energy | A mixture of toluene and each compound (1 milligram (mg) of each compound was dissolved in 3 cubic centimeters (cc) toluene) was added to a quartz cell and then nitrogen (N) (at 77 Kelvins, K) was added thereto. A photoluminescence measuring apparatus was used to measure photoluminescence spectra, and the photoluminescence spectra were compared with those at room temperature to analyze only the peaks that are observed at a low temperature and calculate the $T_1$ energy level. |
| Method of measuring maximum emission wavelength | The compounds were diluted in toluene to a concentration of 10 millimolar (mM) and an ISC PC1 spectrofluorometer loaded with a xenon (Xe) lamp was used to measure photoluminescence (PL) of the compounds in a solution. |

TABLE 2

| Compound No. | HOMO (electron volt, eV) | LUMO (eV) | $T_1$ energy level (eV) | Maximum emission wavelength (nm) |
|---|---|---|---|---|
| 1 | −5.21 | −1.47 | 2.49 | 498 |
| 2 | −5.51 | −1.49 | 2.51 | 494 |
| 3 | −6.57 | −3.26 | 2.54 | 489 |
| 4 | −6.18 | −2.58 | 2.62 | 474 |
| 5 | −6.03 | −2.41 | 2.63 | 471 |
| 6 | −5.79 | −2.18 | 2.64 | 469 |
| 7 | −5.65 | −2.04 | 2.65 | 468 |
| 8 | −5.73 | −2.15 | 2.63 | 472 |
| 9 | −5.55 | −1.98 | 2.55 | 486 |
| 12 | −6.05 | −2.48 | 2.62 | 472 |
| 14 | −6.51 | −2.91 | 2.62 | 473 |
| 15 | −6.35 | −2.76 | 2.62 | 473 |
| 17 | 5.93 | 1.47 | 2.78 | 490 |

TABLE 3

| Compound No. | PLQY (%) | X-coordinate | Y-coordinate |
|---|---|---|---|
| 1 | 85 | 0.17 | 0.38 |
| 2 | 82 | 0.17 | 0.37 |
| 3 | 87 | 0.16 | 0.36 |
| 4 | 89 | 0.16 | 0.32 |
| 5 | 90 | 0.16 | 0.31 |
| 6 | 78 | 0.16 | 0.30 |
| 7 | 79 | 0.16 | 0.30 |
| 8 | 75 | 0.16 | 0.32 |
| 9 | 74 | 0.17 | 0.35 |
| 12 | 59 | 0.16 | 0.32 |
| 14 | 69 | 0.16 | 0.31 |
| 15 | 81 | 0.17 | 0.32 |
| 17 | 71 | 0.17 | 0.32 |

It may be concluded from the data shown in Table 2 that the compounds have electrooptical properties that are suitable as a material for an organic light-emitting device.

Evaluation Example 2

Evaluation of Photoluminescence Quantum Yields (PLQY) and Color Coordination

A C$_2$H$_4$Cl$_2$ solution of PMMA and each of the compounds synthesized as described above were mixed (8 percent by weight (wt %)), and mixtures obtained therefrom were coated on a quartz substrate by using a spin coater, heat-treated in an oven at a temperature of 80° C., and cooled to room temperature to obtain films. The films obtained therefrom were used to evaluate PLQY and color coordination of each compound. PLQY and color coordination in a film of the compound were evaluated by using a Hamamatsu Photonics absolute PL quantum yield measurement system loaded with a Xe light source, a monochromator, a photonic multichannel analyzer, and an integrating sphere, and using PLQY measurement software (Hamamatsu Photonics, Ltd., Shizuoka, Japan). The same processes were repeated for other compounds and PLQY and a color coordination film obtained therefrom are shown in Table 3 below.

It may be concluded from the data shown in Table 3 that the compounds have electrooptical properties that are suitable as a material for an organic light-emitting device.

As described above, according to the one or more of the above embodiments, the organometallic compounds have excellent electrical properties and thermal stability and thus, an organic light-emitting device including the organometallic compounds may have a low driving voltage, high efficiency, high brightness, and a long lifespan.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:

1. An organometallic compound represented by Formula 1,

Formula 1
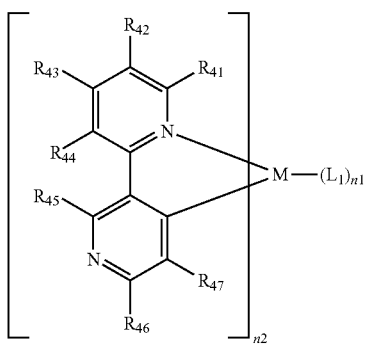
wherein
$L_1$ in Formula 1 comprises at least one selected from a first ligand represented by Formulae 2A-1 to 2A-27 and 2A-29 to 2A-45, a second ligand represented by Formula 2B, and a third ligand represented by one selected from Formulae 2C, 2D, and 2E:
Formula 2A-1
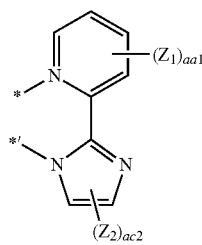
Formula 2A-2
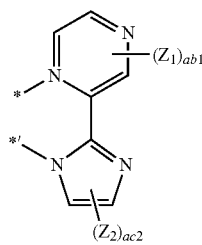
Formula 2A-3
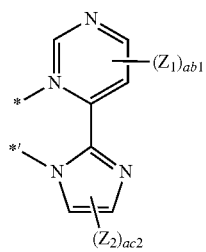
Formula 2A-4
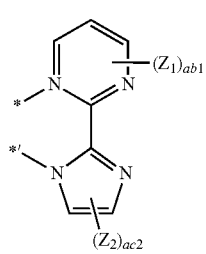
Formula 2A-5
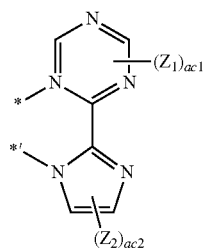
Formula 2A-6
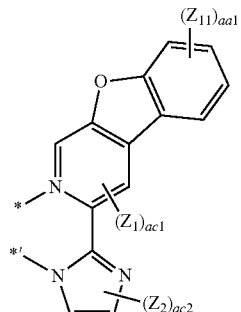
Formula 2A-7
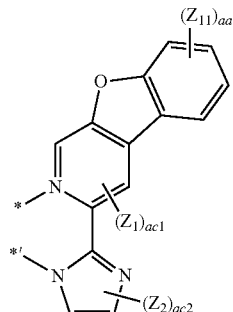
Formula 2A-8
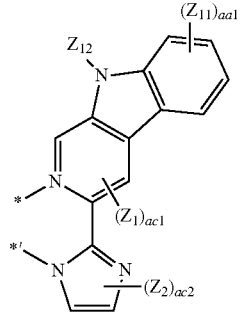
Formula 2A-9
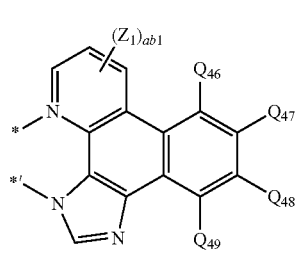

Formula 2A-10
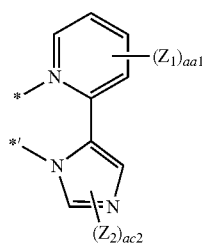
Formula 2A-11
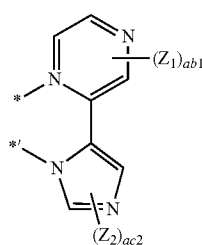
Formula 2A-12
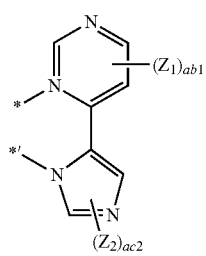
Formula 2A-13
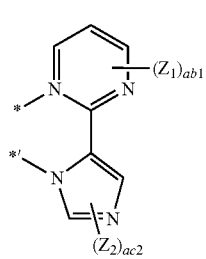
Formula 2A-14
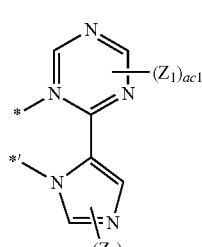
Formula 2A-15
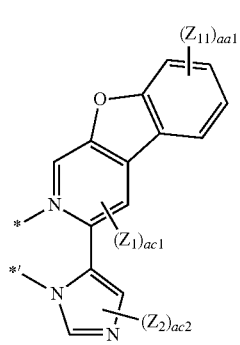
Formula 2A-16
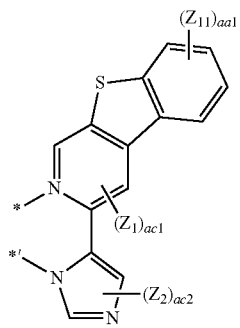
Formula 2A-17
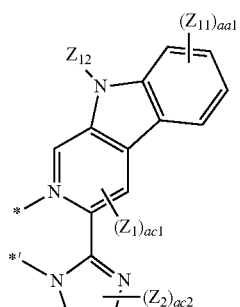
Formula 2A-18
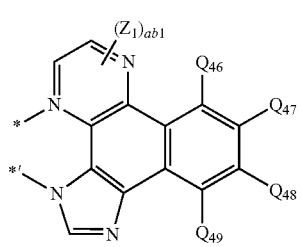
Formula 2A-19
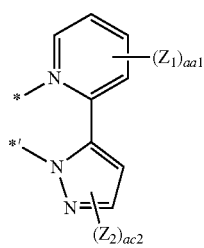
Formula 2A-20
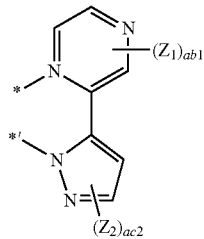
Formula 2A-21
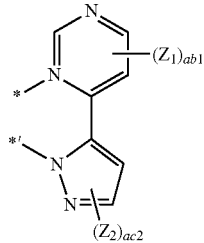

Formula 2A-22
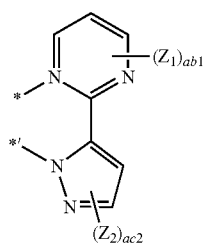
Formula 2A-23
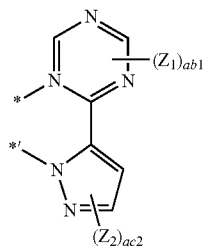
Formula 2A-24
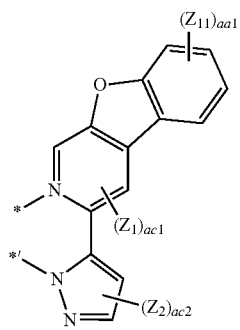
Formula 2A-25
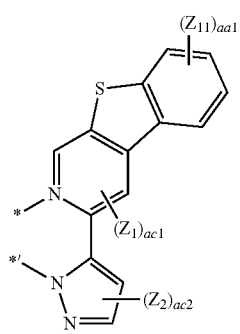
Formula 2A-26
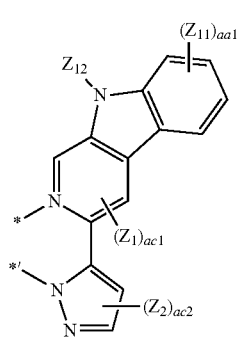
Formula 2A-27
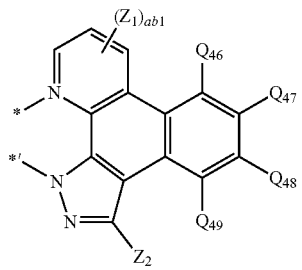
Formula 2A-29
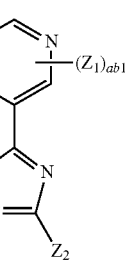
Formula 2A-30
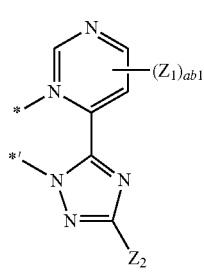
Formula 2A-31
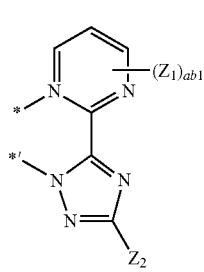
Formula 2A-32
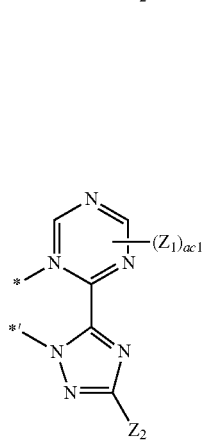

Formula 2A-33
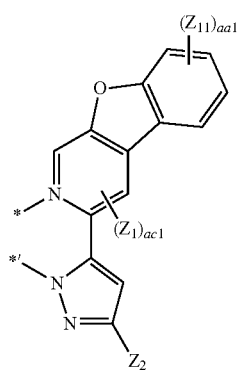
Formula 2A-34
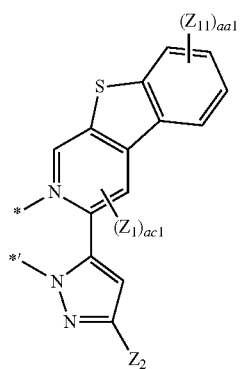
Formula 2A-35
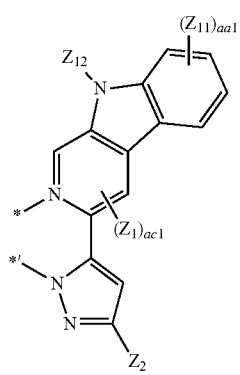
Formula 2A-36
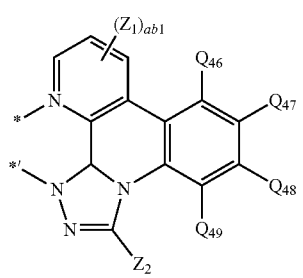
Formula 2A-37
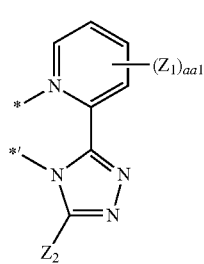
Formula 2A-38
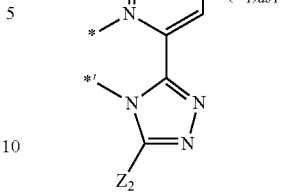
Formula 2A-39
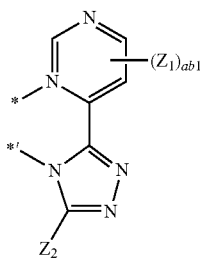
Formula 2A-40
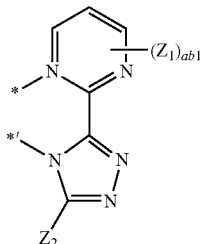
Formula 2A-41
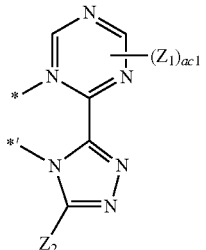
Formula 2A-42
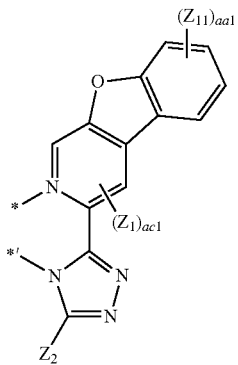

-continued

Formula 2A-43

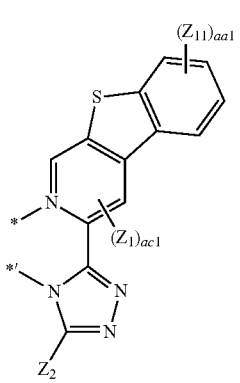

Formula 2A-44

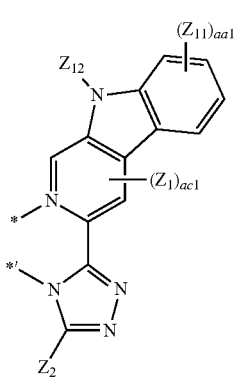

Formula 2A-45

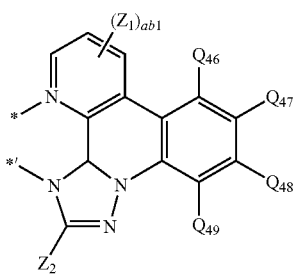

wherein, in Formulae 2A-1 to 2A-45, $Z_1$, $Z_2$, $Z_{11}$ to $Z_{13}$, and $Q_{46}$ to $Q_{49}$ are each independently selected from a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, —SF$_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a pyridinyl group, and a pyrimidinyl group;

a phenyl group, a naphthyl group, a fluorenyl group, a phenantherenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, an isothizolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a guinolinyl group, an isoguinolinyl group, a benzoguinolinyl group, a guinoxalinyl group, a guinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a guinolinyl group, an isoguinolinyl group, a benzoguinolinyl group, a guinoxalinyl group, a guinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, squonic acid group or a salt thereof, phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a guinolinyl group, an isoguinolinyl group, a benzoguinolinyl group, a guinoxalinyl group, a guinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

aa1 is an integer selected from 1 to 4;

ab1 and ab2 are each independently integers selected from 1 to 3;

ac1 and a02 are each independently 1 or 2; and

* and *' are binding sites to M in Formula 1,

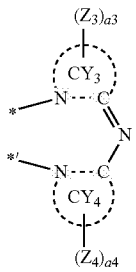

Formula 2B

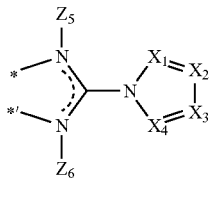

Formula 2C

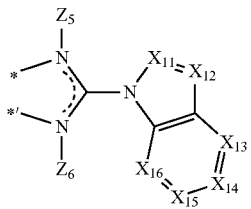

Formula 2D

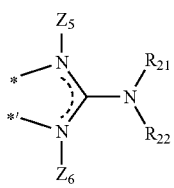

Formula 2E

*——$(Z_{32})_{b2}$——*'

Formula 3 in Formulae 1, 2B to 2E, and 3 above,

M is selected from Ir, Pt, Os, Ti, Zr, Hf, Eu, Tb, and Tm;

$CY_3$ and $CY_4$ are each independently a $C_2$-$C_{60}$ heterocyclic group comprising at least one N;

$X_1$ is N or $CR_1$, $X_2$ is N or $CR_2$, $X_3$ is N or $CR_3$, $X_4$ is N or $CR_4$, $X_{11}$ is N or $CR_{11}$, $X_{12}$ is N or $CR_{12}$, $X_{13}$ is N or $CR_{13}$, $X_{14}$ is N or $CR_{14}$, $X_{15}$ is N or $CR_{15}$, and $X_{16}$ is N or $CR_{16}$;

$Z_{32}$ is selected from *—O—*', *—S—*', *—N($Q_{51}$)—*', *—C($Q_{52}$)($Q_{53}$)—*', *—C($Q_{54}$)=C($Q_{55}$)—*', and

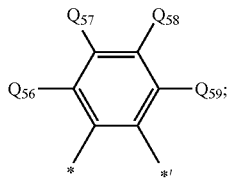

b2 is an integer selected from 1 to 10, and when b2 is 2 or greater, groups $Z_{32}$ are the same or different;

$R_{41}$ to $R_{47}$, $Z_3$ to $Z_6$, $R_1$ to $R_4$, $R_{11}$ to $R_{16}$, and $Q_{51}$ to $Q_{59}$ are each independently selected from a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

$R_{21}$ and $R_{22}$ are each independently selected from a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed heteropolycyclic group; and $R_{21}$ and $R_{22}$ optionally bind to each other via a single bond or a second linking group represented by Formula 3; provided that the following conditions regarding $R_{21}$ and $R_{22}$ in Formula 2E are excluded i) where $R_{21}$ and $R_{22}$ are both phenyl groups, ii) where $R_{21}$ and $R_{22}$ are both phenyl groups substituted with a tert-butyl group, iii) where $R_{21}$ and $R_{22}$ are both ethyl groups, iv) where $R_{21}$ and $R_{22}$ are both propyl groups, v) where $R_{21}$ and $R_{22}$ are both butyl groups, and vi) where $R_{21}$ and $R_{22}$ are both —Si($CH_3$)$_3$;

in Formula 1, both $R_{45}$ and $R_{46}$ are not —F;

in Formula 1, when $L_1$ includes the second ligand or the third ligand, each of $R_{41}$ to $R_{47}$ is not a hydrogen;

in Formula 2D, at least one selected from $X_{11}$ to $X_{16}$ is N;

a1 to a4 are each independently integers selected from 1 to 5;

n1 is an integer selected from 1 or 2;

n2 is an integer selected from 1 or 2;

* and *' are binding sites to M in Formula 1;

in Formula 2B, a bond between C and N are each independently a single bond or a double bond;

at least one substituent of the substituted $C_1$-$C_{60}$ alkyl group, the substituted $C_2$-$C_{60}$ alkenyl group, substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, substituted $C_6$-$C_{60}$ aryl group, the substituted $C_6$-$C_{60}$ aryloxy group, substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

$C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$); wherein, $Q_1$ to $Q_7$, $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

2. The organometallic compound of claim 1, wherein $CY_1$ to $CY_4$ are each independently selected from a pyrrole, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a benzimidazole, a benzoxazole, an iso-benzoxazole, a triazole, a tetrazole, an oxadiazole, a triazine, a pyridoindole, a pyridofuran, and a pyridothiophene.

3. The organometallic compound of claim 1, wherein in Formula 2C above, at least one of $X_1$ to $X_4$ is N.

4. The organometallic compound of claim 1, wherein $R_{41}$ to $R_{47}$, $Z_1$ to $Z_6$, $R_1$ to $R_4$, $R_{11}$ to $R_{16}$, and $Q_{51}$ to $Q_{59}$ are each independently selected from a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, —SF$_5$, a $C_1$-$C_{60}$ alkyl group, a $C_2$-$C_{60}$ alkenyl group, a $C_2$-$C_{60}$ alkynyl group and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a pyridinyl group, and a pyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group(phenazinyl), a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_1$-$C_{60}$ alkyl group substituted with at least one —F, a $C_1$-$C_{60}$ alkoxy group substituted with at least one —F, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —N($Q_{31}$)($Q_{32}$), —Si($Q_{33}$)($Q_{34}$)($Q_{35}$), and —B($Q_{36}$)($Q_{37}$); and —N($Q_1$)($Q_2$), —Si($Q_3$)($Q_4$)($Q_5$), and —B($Q_6$)($Q_7$); wherein, $Q_1$ to $Q_7$ and $Q_{31}$ to $Q_{37}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group.

5. The organometallic compound of claim 1, wherein $R_{41}$ to $R_{47}$, $Z_1$ to $Z_6$, $R_1$ to $R_4$, $R_{11}$ to $R_{16}$, and $Q_{51}$ to $Q_{59}$ are each independently selected from a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, —SF$_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a $C_1$-$C_{20}$ alkyl group substituted with at least one —F, a $C_1$-$C_{20}$ alkoxy group substituted with at least one —F, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group.

6. The organometallic compound of claim 1, wherein $R_{41}$ to $R_{47}$, $Z_1$ to $Z_6$, $R_1$ to $R_4$, $R_{11}$ to $R_{16}$, and $Q_{51}$ to $Q_{59}$ are each independently selected from a hydrogen, —F, a cyano group, a nitro group, —SF$_5$, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group; and a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group, each substituted with at least one selected from —F, a cyano group, and a nitro group.

7. The organometallic compound of claim 1, wherein in Formula 1, at least one of $R_{45}$ and $R_{46}$ is not a hydrogen.

8. The organometallic compound of claim 1, wherein in Formula 1, $R_{45}$ and $R_{46}$ are different.

9. The organometallic compound of claim 1, wherein the second ligand is represented by any one of Formulae 2B-1 to 2B-25.

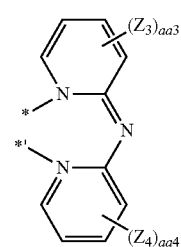

Formula 2B-1

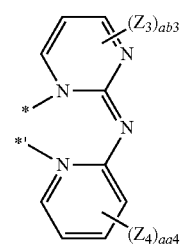

Formula 2B-2

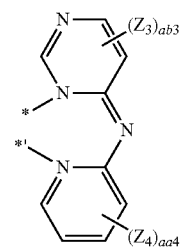

Formula 2B-3

-continued

Formula 2B-4

Formula 2B-5

Formula 2B-6

Formula 2B-7

Formula 2B-8

Formula 2B-9

-continued

Formula 2B-10

Formula 2B-11

Formula 2B-12

Formula 2B-13

Formula 2B-14

Formula 2B-15

-continued

Formula 2B-16
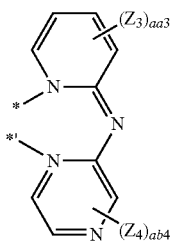

Formula 2B-17
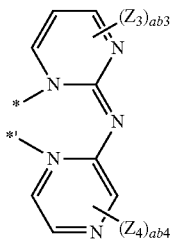

Formula 2B-18
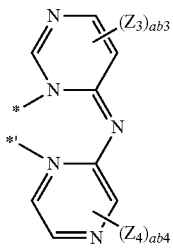

Formula 2B-19
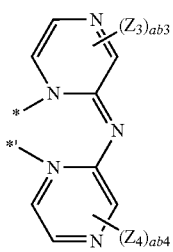

Formula 2B-20
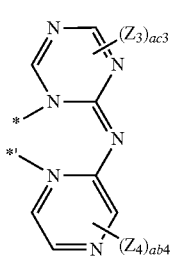

Formula 2B-21
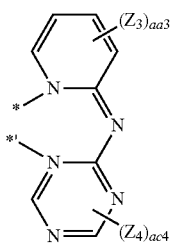

Formula 2B-22
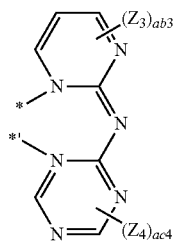

Formula 2B-23
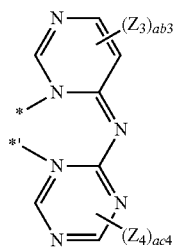

Formula 2B-24
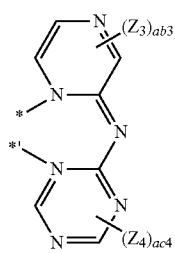

Formula 2B-25
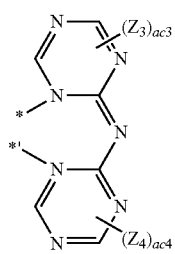

in Formulae 2B-1 to 2B-25, $Z_3$ and $Z_4$ are each independently a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, —SF$_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isoihiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

aa3 and aa4 are each independently integers selected from 1 to 4;

ab3 and ab4 are each independently integers selected from 1 to 3;

ac3 and ab4 are each independently integers of 1 or 2; and

* and *' are binding sites to M in Formula 1.

10. The organometallic compound of claim 1, wherein the third ligand is represented by any one of Formulae 2C-1 to 2C-4 and 2D-1 to 2D-4:

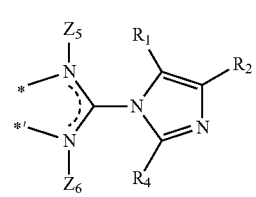

Formula 2C-1

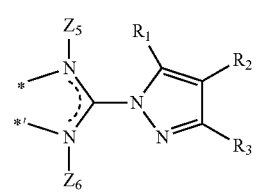

Formula 2C-2

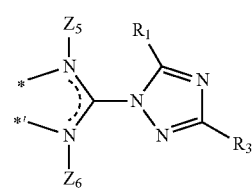

Formula 2C-3

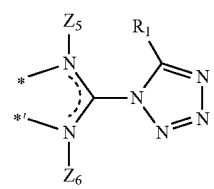

Formula 2C-4

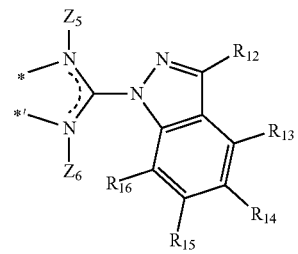

Formula 2D-1

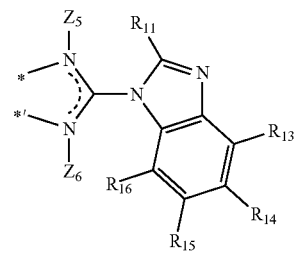

Formula 2D-2

-continued

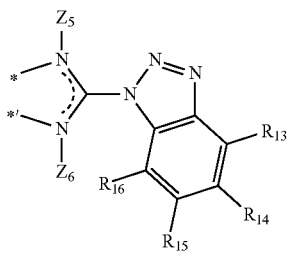

Formula 2D-3

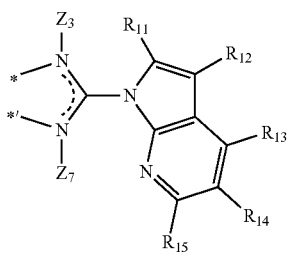

Formula 2D-4 in Formula 2C-1 to 2C-4 and 2D-1 to 2D-4, $Z_5$, $Z_6$, $R_1$ to $R_4$, and $R_{11}$ to $R_{16}$ are each independently selected from a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and

* and *' are binding sites to M.

11. The organometallic compound of claim 1, wherein in Formula 2E, $R_{21}$ and $R_{22}$ are each independently selected from a cyano group;

a $C_1$-$C_{20}$ alkyl group substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a pyridinyl group, and a pyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a penlaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyndinyl group, and an imidazopyrimidinyl group; wherein, $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, and a quinoxalinyl group;

at least one selected from $R_{21}$ and $R_{22}$ is selected from a cyano group;

a $C_1$-$C_{20}$ alkyl group substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a pyridinyl group, and a pyrimidinyl group;

a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a C1-C20 alkyl group, a C1-C20 alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group.

12. The organometallic compound of claim 1, wherein the third ligand is represented by Formula 2E(1) or 2E(2):

Formula 2E(1)

Formula 2E(2)

in Formula 2E(1) and 2E(2), descriptions of $Z_5$, $Z_6$, $Z_{32}$, and b2 are the same as described in claim 1, $X_{31}$ is N or $CR_{31}$,
$X_{32}$ is N or $CR_{32}$,
$X_{33}$ is N or $CR_{33}$,
$X_{34}$ is N or $CR_{34}$,
$X_{35}$ is N or $CR_{35}$,
$X_{36}$ is N or $CR_{36}$,
$X_{37}$ is N or $CR_{37}$,
$X_{38}$ is N or $CR_{38}$, and
at least one of $X_{31}$ to $X_{38}$ is N; and
$R_{31}$ to $R_{38}$ are each independently the same as described for $R_1$.

13. The organometallic compound of claim 1, wherein the third ligand is represented by any one of Formulae 2E-1 to 2E-25:

Formula 2E-1

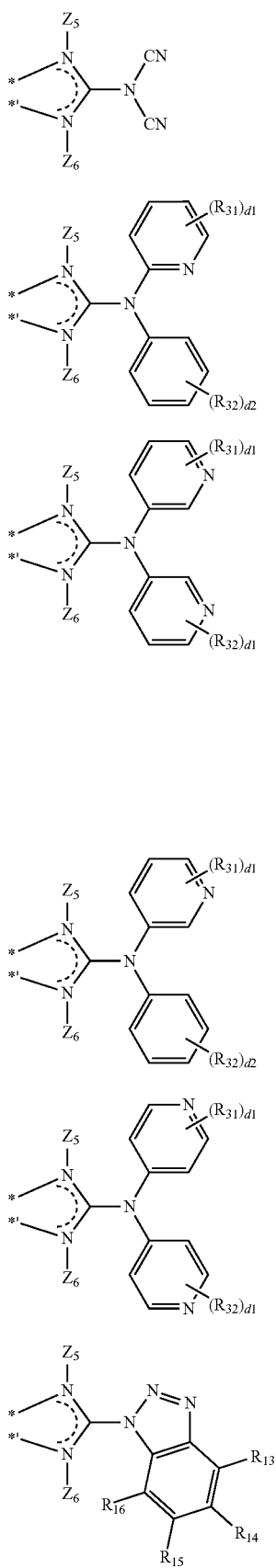
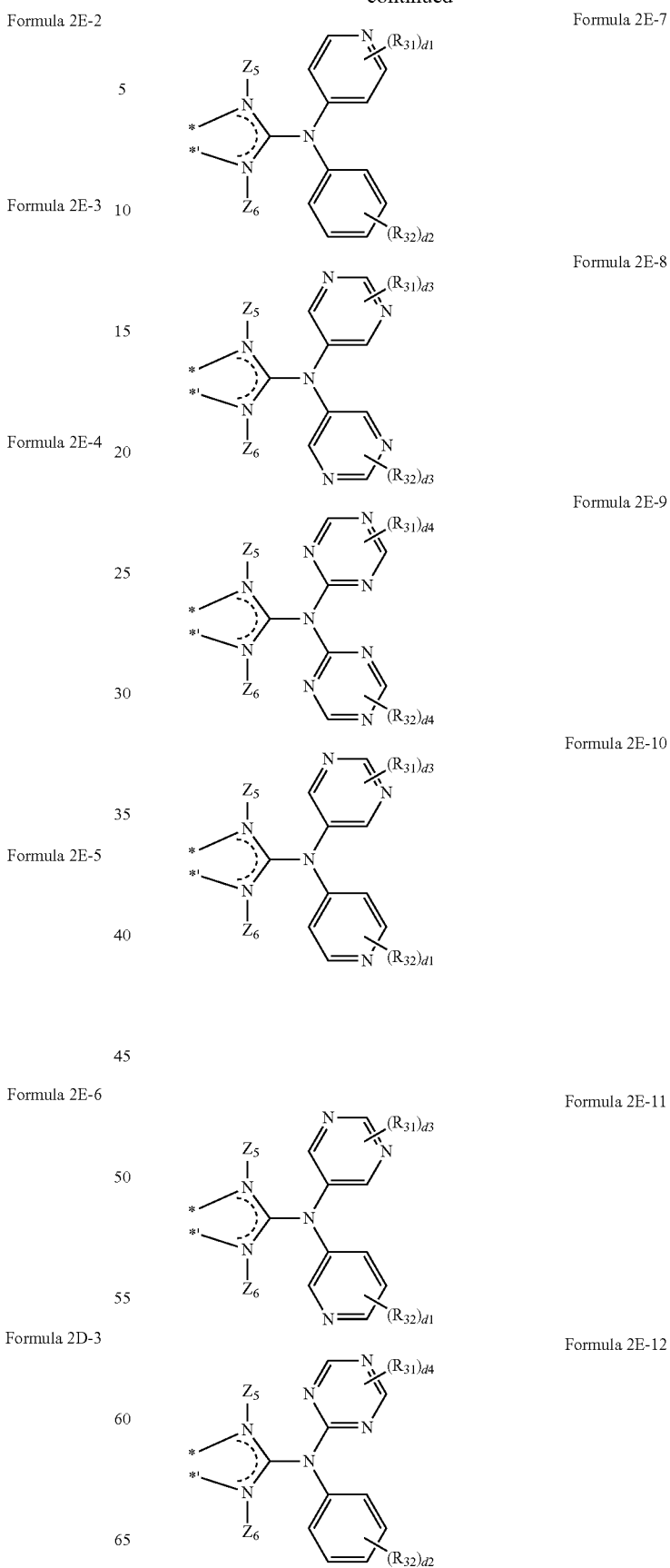

-continued
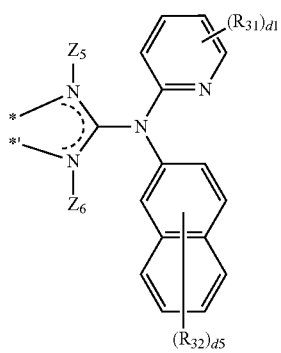
Formula 2E-13
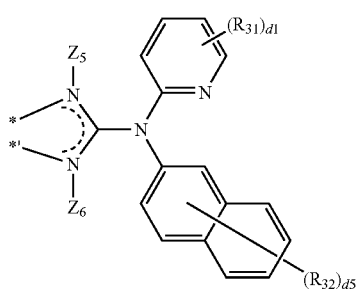
Formula 2E-14
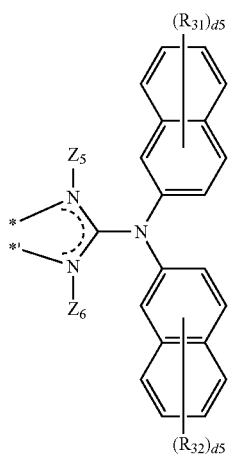
Formula 2E-15
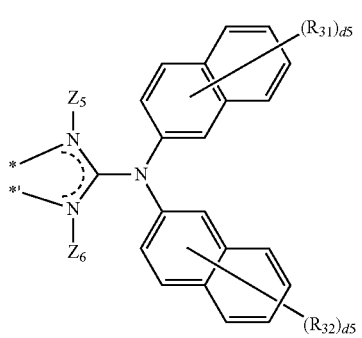
Formula 2E-16
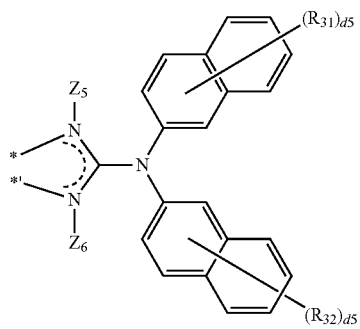
Formula 2E-16
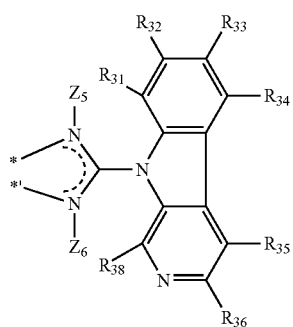
Formula 2E-17
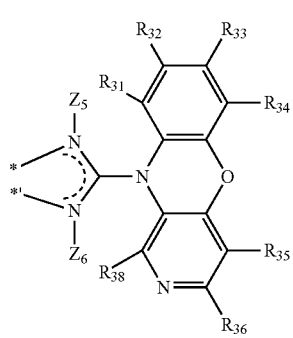
Formula 2E-18
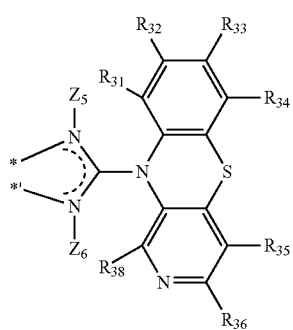
Formula 2E-19
Formula 2E-20

-continued

Formula 2E-21

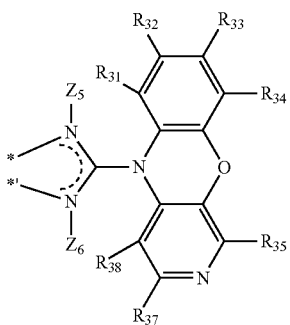

Formula 2E-22

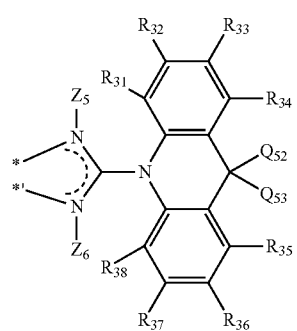

Formula 2E-23

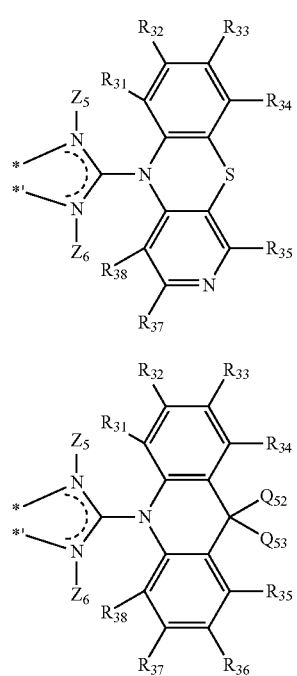

Formula 2E-24

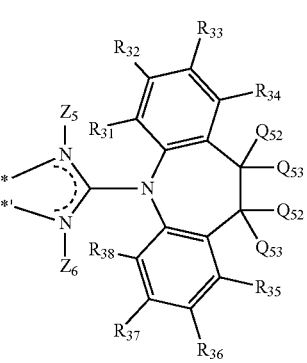

Formula 2E-25

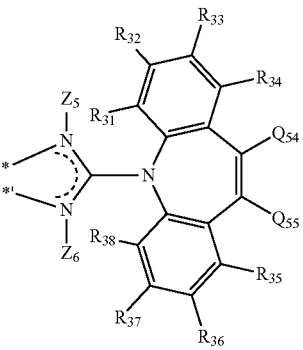

in Formulae 2E-1 to 2E-25, $Z_5$, $Z_6$, $R_{31}$ to $R_{38}$, and $Q_{52}$ to $Q_{55}$ above are each independently selected from a hydrogen, a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, carboxylic acid group or a salt thereof, sulfonic acid group or a salt thereof, phosphoric acid group or a salt thereof, a C1-C20 alkyl group, a C1-C20 alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —N($Q_1$)($Q_2$), —Si($Q_3$)($Q_4$)($Q_5$), and —B($Q_6$)($Q_7$); wherein, $Q_1$ to $Q_7$ are each independently selected from hydrogen, a $C_1$-$C_{20}$ alkyl group, a $C_1$-$C_{20}$ alkoxy group, a phenyl group, and a naphthyl group;

d1 is an integer selected from 1 to 4;

d2 is an integer selected from 1 to 5;

d3 is an integer selected from 1 to 3;

d4 is 1 or 2; and d5 is an integer selected from 1 to 7.

14. The organometallic compound of claim 1, wherein the n1 is 1.

15. An organometallic compound is represented by Formula 1A:

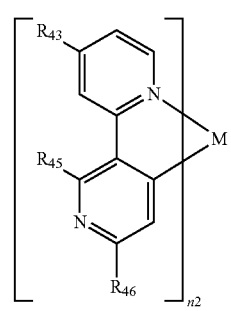

Formula 1A in Formula 1A, $R_{43}$ is selected from a hydrogen, —F, a cyano group, a nitro group, —$SF_5$, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group and a triazinyl group; and a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group and a triazinyl group, each substituted with at least one selected from —F, a cyano group, and a nitro group; and $R_{45}$ and $R_{46}$ are each independently selected from a hydrogen, —F, a cyano group, a nitro group, —$SF_5$, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group and a triazinyl group; and a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group and a triazinyl group, each substituted with at least one selected from —F, a cyano group, and a nitro group; wherein at least one of $R_{45}$ and $R_{46}$ is selected from a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group and a triazinyl group, each substituted with —F; and n2 is 2 or 3.

16. The organometallic compound of claim 1, wherein
n1 is 1 or 2;
$L_1$ is selected from a ligand represented by Formula 2A-19, a ligand represented by Formula 2B-1, and a ligand represented by Formula 2E-17:

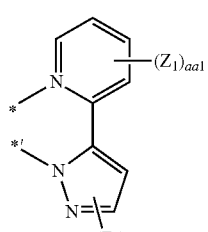

Formula 2A-19

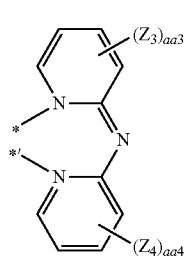

Formula 2B-1

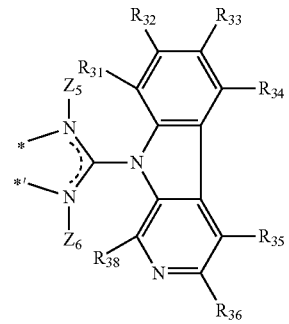

Formula 2E-17

In Formulae 2A-19, 2B-1, and 2E-17,
$Z_1$ to $Z_6$, $R_{31}$ to $R_{36}$, and $R_{38}$ are each independently selected from
a hydrogen, —F, a cyano group, a nitro group, —SF$_5$, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group; and
a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group and a triazinyl group, each substituted with at least one selected from —F, a cyano group, and a nitro group, and
aa1, aa3, aa4, and ac2 are each independently 1 or 2.

17. An organometallic compound selected from Compounds 4 to 9 and 14 to 22:

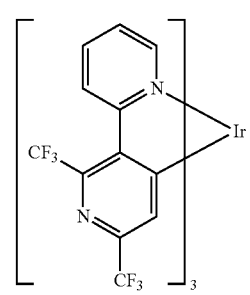

4

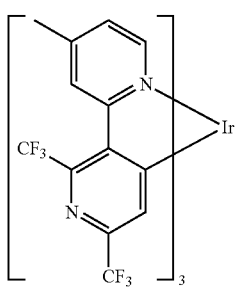
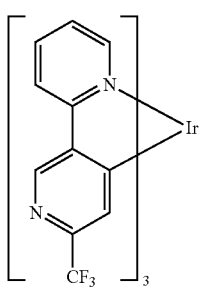
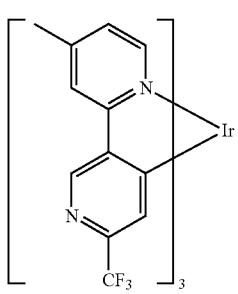
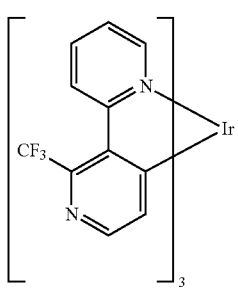
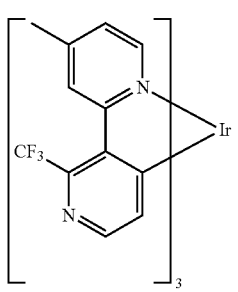
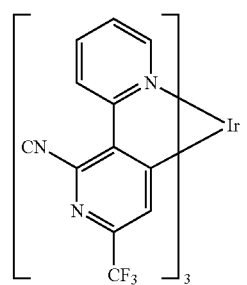
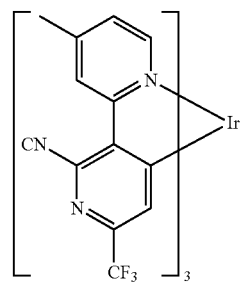
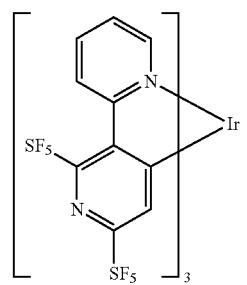
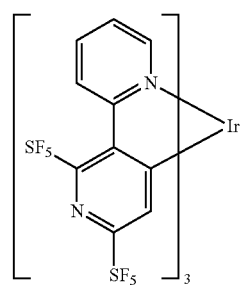
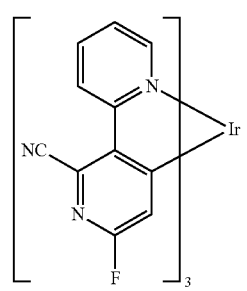

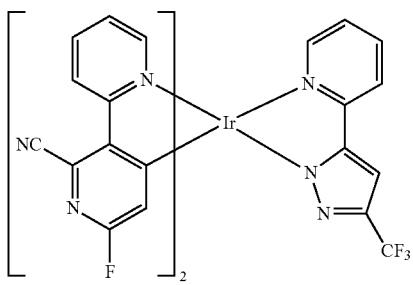

18

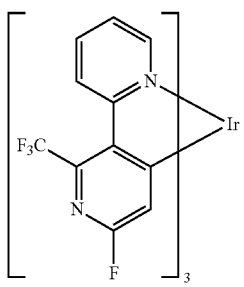

19

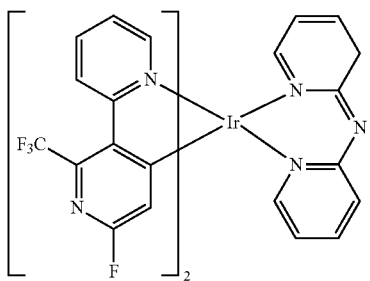

20

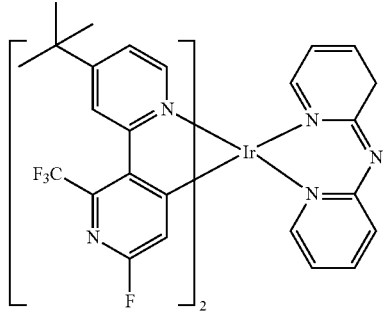

21

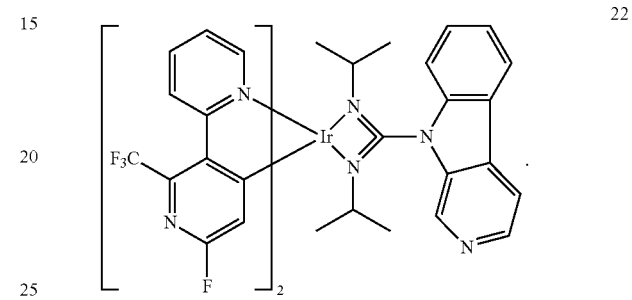

22

18. An organic light-emitting device comprising
a first electrode;
a second electrode; and
an organic layer disposed between the first electrode and the second electrode, wherein the organic layer comprises an emission layer and the organometallic compound of claim 1.

19. The organic light-emitting device of claim 18, wherein the organic light-emitting device emits blue light having a maximum emission wavelength in a range of about 440 nanometers to about 500 nanometers, an x-color coordinate in a range of about 0.16 to about 0.22, and a y-color coordinate in a range of about 0.10 to about 0.40.

* * * * *